United States Patent [19]
Margolis et al.

[11] Patent Number: 6,045,797
[45] Date of Patent: Apr. 4, 2000

[54] TREATMENT OR DIAGNOSIS OF DISEASES OR CONDITIONS ASSOCIATED WITH A BLM DOMAIN

[75] Inventors: Ben Lewis Margolis; Joseph Schlessinger, both of New York, N.Y.

[73] Assignee: New York University Medical Center, New York City, N.Y.

[21] Appl. No.: 08/866,381

[22] Filed: May 30, 1997

Related U.S. Application Data

[63] Continuation of application No. 08/522,539, Sep. 1, 1995, abandoned, which is a continuation of application No. 08/212,234, Mar. 14, 1994, abandoned.

[51] Int. Cl.⁷ .............................. A61K 39/00; C07K 1/00
[52] U.S. Cl. ........................ 424/185.1; 514/12; 530/350
[58] Field of Search ................................. 530/324, 350; 514/2, 12; 435/69.1; 424/185.1

[56] References Cited

U.S. PATENT DOCUMENTS

| | | | |
|---|---|---|---|
| 3,691,016 | 9/1972 | Patel | 195/68 |
| 3,969,287 | 7/1976 | Jaworek et al. | 260/8 |
| 4,195,128 | 3/1980 | Hildebrand et al. | 435/178 |
| 4,215,051 | 7/1980 | Schroeder et al. | 260/346.7 |
| 4,229,537 | 10/1980 | Hodgins et al. | 435/177 |
| 4,247,642 | 1/1981 | Hirohara et al. | 435/178 |
| 4,330,440 | 5/1982 | Ayers et al. | 525/54.31 |
| 4,376,110 | 3/1983 | David et al. | 436/513 |
| 4,946,778 | 8/1990 | Ladner et al. | 435/69.6 |

FOREIGN PATENT DOCUMENTS

| | | |
|---|---|---|
| 92/03476 | 3/1992 | WIPO . |
| 92/22339 | 11/1993 | WIPO . |
| 9323569 | 11/1993 | WIPO . |

OTHER PUBLICATIONS

Margolis, B. et al, "The SH2 domain protein, GRB–7, is amplified, overexpressed, and in a tight complex with HER2 in breast cancer," *Journal of Cellular Biochemistry Supplement*, 18B: 1331–1340 (1994).
Aaronson, *Science*, 254:1146–1153 (1991).
Adelman et al., *DNA*, 2:183–193 (1983).
Bargmann et al., *Nature*, 319:226–230 (1986).
Bird, *Science*, 242:423–426 (1988).
Bitter et al., *Methods in Enzymol.*, 153:516–544 (1987).
Colberre–Garapin et al., *J. Mol. Biol.*, 150:1–14 (1981).
Cole et al., *Monoclonal Antibodies and Cancer Therapy*, Alan R. Liss, Inc., pp. 77–96 (1985).
Cote et al., *Proc. Natl. Acad. Sci. USA*, 80:2026–2030 (1983).
Domchek et al., *Biochemistry*, 31:9865–9870 (1992).
Fantl et al., *Cell*, 69:413–422 (1992).
Felder et al., *Mol. Cell. Biol.*, 13:1449–1455 (1993).
Felgner and Ringold, *Nature*, 337:387–388 (1989).
Fingl and Woodbury, *The Pharmacological Basis of Therapeutics*, Ch. 1, pp. 1–46 (1975).
Fry et al., *Protein Science*, 2:1785–1797 (1993).
Hardie, *Symp. Soc. Exp. Biol.*, 44:241–255 (1990).
Hunter, *Cell*, 64:249–270 (1991).
Huse et al., *Science*, 246:1275–1281 (1989).
Huston et al., *Proc. Natl. Acad. Sci. USA*, 85:5879–5883 (1988).
Inouye and Inouye, *Nucleic Acids Res.*, 13:3101–3109 (1985).
Kozbor and Roder, *Immunology Today*, 4:72–79 (1983).
Koch et al., *Science*, 252:668–674 (1991).
Köhler and Milstein, *Nature*, 256:495–497 (1975).
Lam et al., *Nature*, 354:82–84 (1991).
Logan and Shenk, *Proc. Natl. Acad. Sci. USA*, 81:3655–3659 (1984).
Lowenstein et al., *Cell*, 70:431–442 (1992).
Lowy et al., *Cell*, 22:817–823 (1980).
Manser and Wood, *Developmental Genetics*, 11:49–64 (1990).
Marasco et al., *Proc. Natl. Acad. Sci. USA*, 90:7889–7893 (1993).
Margolis et al., *Proc. Natl. Acad. Sci. USA*, 89:8894–8898 (1992).
Margolis, *Cell Growth & Differ.*, 3:73–80 (1992).
Millauer et al., *Nature* 367:576–579 (1994).
Morrison et al., *Proc. Natl. Acad. Sci. USA*, 81:6851–6855 (1984).
Mulligan and Berg, *Proc. Natl. Acad. Sci. USA*, 78:2072–2079 (1981).
Musacchio et al., *TIBS*, 18:342–348 (1993).
Neuberger et al., *Nature*, 312:604–608 (1984).
O'Hara et al., *Proc. Natl. Acad. Sci. USA*, 78:1527–1531 (1981).
Padhy et al., *Cell*, 28:865–871 (1982).
Pawson and Schlessinger, *Current Biol.*, 13:434–442 (1993).
Pawson and Gish, *Cell*, 71:359–362 (1992).
Pendergrast et al., *Cell*, 75:175–185 (1993).
Posada and Cooper, *Mol. Biol. Cell*, 3:583–592 (1992).
Rotin et al., *EMBO Journal*, 11:559–597 (1992).
Rüther and Müller–Hill, *EMBO Journal*, 2:1791–1794 (1983).

(List continued on next page.)

*Primary Examiner*—Patricia A. Duffy
*Attorney, Agent, or Firm*—Lyon & Lyon LLP

[57] ABSTRACT

A method for treatment of a disease or condition in an organism characterized by an abnormal level of interaction between a BLM domain and its natural binding partner is described. The disease or condition may also be characterized by an abnormality in a signal transduction pathway, wherein the pathway contains a protein with a BLM domain. The method includes disrupting or promoting that interaction (or signal) in vivo. The method also involves inhibiting the activity of the complex formed between the BLM domain-containing protein and its natural binding partner. A method for diagnosis of such a disease or condition by detecting the level of such interaction as an indication of that disease or condition is also described. Also, a method for screening for an agent useful for treatment of such a disease or condition by assaying potential agents for the ability to disrupt or promote that interaction is described. The invention also features a peptide comprising, consisting or consisting essentially of a BLM domain.

8 Claims, 8 Drawing Sheets

OTHER PUBLICATIONS

Sadowski et al., *Mol. Cell. Biol.*, 6:4396–4408 (1986).
Santerre et al., *Gene*, 30:147–156 (1984).
Schechter et al. *Nature*, 312:513–516 (1984).
Schlessinger and Ullrich, *Neuron*, 9(3):383–391 (1992).
Skolnik et al., *Cell*, 65:83–90 (1991).
Slamon et al., *Science*, 244:707–712 (1989).
Slamon et al., *Science*, 235:177–182 (1987).
Smith et al., *J. Viol.*, 46:584–593 (1983).
Songyang et al., *Cell*, 72:767–778 (1993).
Stahl, *Nature* 332:269–272 (1988).
Stein et al., *EMBO Journal*, 13(6):1331–1340 (1994).
Szybalska and Szybalski, *Proc. Natl. Acad. Sci. USA*, 48:2026–2034 (1962).
Takeda et al., *Nature*, 314:452–454 (1985).
Ullrich and Schlessinger, *Cell*, 61:203–212 (1990).
Van Heeke and Schuster, *J. Biol. Chem.*, 264:5503–5509 (1989).
Wigler et al., *Proc. Natl. Acad. Sci. USA*, 77:3567–3570 (1980).
Wigler et al., *Cell*, 11:223–232 (1977).
Yamamoto et al., *Nature*, 319:521–527 (1986).

Alignment of the BLM domain of GRB-7, GRB-10 AND F10E9.6

| | | | | | | | |
|---|---|---|---|---|---|---|---|
| GRB-7 | (95) | pRDssRLc.v | VKVYSEDGac | RsVEVaagaT | ARhVCeMLVq | RaHaLsDESW | |
| GRB-10 | (189) | .mEklRLRkd | VKVFSEDGts | KvVEIltdmT | ARDLCqLLVy | KsHcVdDnSW | |
| F10E9.6 | (187) | .KEakvtKif | VKfFvEDGea | lqLIIderwT | vaDtlkqLae | KnHialmEdh | |
| Consensus | | --e------ | VK-f-EDG-- | --v-i----T | --------L-- | k-H------ | |
| | | | | | | | |
| GRB-7 | (143) | gLVEsHPyLa | LERgLEDHEf | VVEVqeaWPv | ggDSRFIFRK | NFAKYELFKs | |
| GRB-10 | (238) | tLVEhHPqLg | LERcLEDHEi | VVqVestmP. | .SESKFLFRK | NYAKYEFFKn | |
| F10E9.6 | (236) | cIVEeyPeLy | IkRvyEDHEk | VVEnigmWvq | dSpnKLyFmR | rpdKYaFisr | |
| Consensus | | -IVE-P-L- | l-R--EDHE- | VV-------- | ----f-F-k | ---KY-f--- | |
| | | | | | | | |
| GRB-7 | (193) | PphtLFPEKM | VssCldaqtG | isheDLIQNF | L......Nag | SfPEIQGFLQ | |
| GRB-10 | (286) | Pvn.FFPDqM | VnwCqqsnGG | ..qapVLQNF | L......Nts | ScPEIQGFLQ | |
| F10E9.6 | (286) | PeLyLLtpKt | sdhmeipsGd | qwtiDVkQkF | Vseyfhrepv | vpPEmeGFLy | |
| Consensus | | P---lf--- | ---------- | ----l-Q-F | l--------- | --PE--GFL- | |
| | | | | | | | |
| GRB-7 | (237) | LRgsGRgSgr | klWKRFFcfL | RRSGLYYSTK | GTSKDPRHLQ | YVADVnESnV | |
| GRB-10 | (327) | VKevGRKS.. | ..WKKLYvcL | RRSGLYYSTK | GTSKEPRHLQ | lLADLeESsI | |
| F10E9.6 | (336) | LKsdGRKS.. | ..WKKhYfvL | RpSGLYYapK | skkpttKdLt | CLmnLhsnqV | |
| Consensus | | lk--GR-S-- | --WKk-y--L | R-SGLYY--K | -------r-L- | -l--l----v | |

Fig. 2A

```
GRB-7       (287)  YvVtqGRKlY  gmPTDFGfCV  KPNKLRnghK  gL.hIFCsED  EQsRTCWLaA
GRB-10      (373)  FyLIaGkKqY  naPnEhGmCI  KPNKaKtemK  eL.RLLCAED  EQiRTCWMtA
F10E9.6     (382)  YtgIgweKkY  ksPTpWcisI  KltaLqmkrs  qFikyICAED  EmtfkkWLvA
Consensus          y-----K-Y   --P-------  K---------  -l---lC-ED  E-----W--A GRB-7       (336)  FRLFKYGvqL  YkNYqqA..Q  sRhLrlsYlg  spPLRSVSDN  tLVAMDFSGH
GRB-10      (422)  FRLLKYGmlL  YqNYrip..Q  RKglppPF..  naPMRSVSEN  SLVAMDFSGq
F10E9.6     (432)  LRIaKnGaeL  leNYerAcqi  RRetlgPass  msaasSstai  SeVphsLShH
Consensus          fRl-K-G--L  --NY------  -r--------  -----S----  --V---fS--

GRB-7       (384)  ........   ..aGRVIDNP  rEALSAAMEE  aqAWRkktnh  rLSLpttcs.
GRB-10      (468)  ........   ..iGRVIDNP  aEAqSAALEE  ghAWRNgStr  mniLsSqspl
F10E9.6     (482)  qrtpsvassi  qlsshmmnNP  thpLSvnV..  ....RNqSpa  sFSVnScqqs
Consensus          ----------  -------NP   ----S-----  ----R-----  ---l------

GRB-7       (421)  .gSsLSAaI
GRB-10      (506)  HPStLnAvI
F10E9.6     (526)  HPSrtSAkL
Consensus          --S---A-i
```

Fig. 2B

Protein sequence of GRB-7 versus GRB-10

```
GRB-7   (2)   ELDLSPTHLSSSPEDVCPTPATP..........................PETPPPPDNPPPG
              ||  |      |   |   | ||                            |
GRB-10  (4)   DINSSVESLNSACNMQSDTDTAPLLEDGQHASNQGAASSSRGQPQASPRQ

GRB-7   (38)  DVKRSQPLPIPSSRKLREEEFQATSLPSIPNPFPELCSPPSQKPILGGSS
               ||||| | |   |  ||| |  ||| ||||||||||  |  |||||||
GRB-10  (54)  KMQRSQPVHILRRLQEEDQQLRTASLPAIPNPFPELTGAAPGSPPSVAPS

GRB-7   (88)  GA........................................
GRB-10 (104)  SLPPPPSQPPAKHCGRCEKWIPGENTRGNGKRKIWRWQFPPGFQLSKLTR

GRB-7   (90)  RGLLPRDSSRLC.....................VVKVYSE
               ||  |   |                        ||| ||
GRB-10 (154)  PGLWTKTTARFSKKQPKNQCPTDTVNPVARMPTSQMEKLRLRKDVKVFSE

GRB-7  (109)  DGACRSVEVAAGATARHVCEMLVQRAHALSDESWGLVESHPYLALERGLE
              ||    ||   |||| ||  | |  |   |||||| || |   |||| ||
GRB-10 (204)  DGTSKVVEILTDMTARDLCQLLVYKSHCVDDNSWTLVEHHPQLGLERCLE
```

Fig. 3A

```
GRB-7   (159)  DHEFVVEVQEAWPVGGDSRFIFRKNFAKYELFKSPPHTLFPEKMVSSCLD
               ||| || ||| ||                ||  |  |
GRB-10  (254)  DHEIVVQVESTMP..SESKFLFRKNYAKYEFFKNPVN.FFPDQMVNWCQQ

GRB-7   (209)  AQTGISHEDLIQNFLNAGSFPEIQGFLQLRGSGRGSGRKLWKRFFCFLRR
                     |||| ||| |   ||||||||  |          |    |||
GRB-10  (301)  SNGG..QAQLLQNFLNTSSCPEIQGFLQVKEVGRKS.....WKKLYVCLRR

GRB-7   (259)  SGLYYSTKGTSKDPRHLQYVADVNESNVYVVVTQGRKLYGMPTDFGFCVKP
               |||||||||||| ||||| |   |  |                 |   |
GRB-10  (345)  SGLYYSTKGTSKEPRHLQLLADLEESSIFYLIAGKKQYNAPNEHGMCIKP

GRB-7   (309)  NKLRNGHKGLHIFCSEDEQSRTCWLAAFRLFKYGVQLYKNYQQAQSRHLR
               || ||| | | |||| ||| ||||| ||||| ||| |||  |   | |
GRB-10  (395)  NKAKTEMKELRLLCAEDEQIRTCWMTAFRLLKYGMLLYQNYRIPQRKGLP

GRB-7   (359)  LSYLGSPPLRSVSDNTLVAMDFSGHAGRVIDNPREALSAAMEEAQAWRKK
                    ||   ||||||| |||||||| ||||||||||   | || | ||
GRB-10  (445)  PPF..NAPMRSVSENSLVAMDFSGQIGRVIDNPAEAQSAALEEGHAWRNG
```

Fig. 3B

```
GRB-7  (409)  TNHRLSLPTTCS..GSSLSAAIHRTQPWFHGRISREESQRLIGQQGLVDG
              ||||||||  |   ||| ||||| |||||||||||||||  | ||||||
GRB-10 (493)  STRMNILSSQSPLHPSTLNAVIHRTQHWFHGRISREESHRIIKQQGLVDG

GRB-7  (457)  VFLVRESQRNPQGFVLSLCHLQKVKHYLILPSEDEGCLYFSMDEGQTRFT
              :| ||:|:||| | |||: ||:|:  ||||:|:| ||||:|||||| ||
GRB-10 (543)  LFLLRDSQSNPKAFVLTLCHHQKIKNFQILPCEDDGQTFFTLDDGNTKFS

GRB-7  (507)  DLLQLVEFHQLNRGILPCLLRHCCARVAL
              ||:|||:|:|||:|||||| |:|  ||||
GRB-10 (593)  DLIQLVDFYQLNKGVLPCKLKHHCIRVAL
```

Fig. 3C

SEQUENCE LISTING (1) GENERAL INFORMATION:

(iii) NUMBER OF SEQUENCES:      6

(2) INFORMATION FOR SEQ ID NO: 1:

(i) SEQUENCE CHARACTERISTICS:
      (A) LENGTH:      335 amino acids
      (B) TYPE:        amino acid
      (C) STRANDEDNESS: single
      (D) TOPOLOGY:    linear (ii) MOLECULE TYPE:   protein (ix) FEATURE:
      (D) OTHER INFORMATION:   BLM domain of GRB-7

(xi) SEQUENCE DESCRIPTION: SEQ ID NO: 1:

```
Pro Arg Asp Ser Ser Arg Leu Cys Val Val Lys Val Tyr Ser Glu Asp
 1               5                  10                  15

Gly Ala Cys Arg Ser Val Glu Val Ala Ala Gly Ala Thr Ala Arg His
            20                  25                  30

Val Cys Glu Met Leu Val Gln Arg Ala His Ala Leu Ser Asp Glu Ser
        35                  40                  45

Trp Gly Leu Val Glu Ser His Pro Tyr Leu Ala Leu Glu Arg Gly Leu
    50                  55                  60

Glu Asp His Glu Phe Val Val Glu Val Gln Glu Ala Trp Pro Val Gly
65                  70                  75                  80

Gly Asp Ser Arg Phe Ile Phe Arg Lys Asn Phe Ala Lys Tyr Glu Leu
                85                  90                  95

Phe Lys Ser Pro Pro His Thr Leu Phe Pro Glu Lys Met Val Ser Ser
               100                 105                 110

Cys Leu Asp Ala Gln Thr Gly Ile Ser His Glu Asp Leu Ile Gln Asn
           115                 120                 125

Phe Leu Asn Ala Gly Ser Phe Pro Glu Ile Gln Gly Phe Leu Gln Leu
       130                 135                 140

Arg Gly Ser Gly Arg Gly Ser Gly Arg Lys Leu Trp Lys Arg Phe Phe
145                 150                 155                 160

Cys Phe Leu Arg Arg Ser Gly Leu Tyr Tyr Ser Thr Lys Gly Thr Ser
               165                 170                 175

Lys Asp Pro Arg His Leu Gln Tyr Val Ala Asp Val Asn Glu Ser Asn
           180                 185                 190
```

```
Val Tyr Val Thr Gln Gly Arg Lys Leu Tyr Gly Met Pro Thr Asp
        195                 200                 205

Phe Gly Phe Cys Val Lys Pro Asn Lys Leu Arg Asn Gly His Lys Gly
210                 215                 220

Leu His Ile Phe Cys Ser Glu Asp Glu Gln Ser Arg Thr Cys Trp Leu
225                 230                 235                 240

Ala Ala Phe Arg Leu Phe Lys Tyr Gly Val Gln Leu Tyr Lys Asn Tyr
        245                 250                 255

Gln Gln Ala Gln Ser Arg His Leu Arg Leu Ser Tyr Leu Gly Ser Pro
        260                 265                 270

Pro Leu Arg Ser Val Ser Asp Asn Thr Leu Val Ala Met Asp Phe Ser
        275                 280                 285

Gly His Ala Gly Arg Val Ile Asp Asn Pro Arg Glu Ala Leu Ser Ala
    290                 295                 300

Ala Met Glu Glu Ala Gln Ala Trp Arg Lys Lys Thr Asn His Arg Leu
305                 310                 315                 320

Ser Leu Pro Thr Thr Cys Ser Gly Ser Ser Leu Ser Ala Ala Ile
                325                 330                 335
```

(2) INFORMATION FOR SEQ ID NO: 2:

(i) SEQUENCE CHARACTERISTICS:
        (A) LENGTH:        326 amino acids
        (B) TYPE:          amino acid
        (C) STRANDEDNESS:   single
        (D) TOPOLOGY:      linear (ii) MOLECULE TYPE:      protein (ix) FEATURE:
        (D) OTHER INFORMATION:   BLM domain of GRB-10

(xi) SEQUENCE DESCRIPTION: SEQ ID NO: 2:

```
Met Glu Lys Leu Arg Leu Arg Lys Asp Val Lys Val Phe Ser Glu Asp
1               5                   10                  15

Gly Thr Ser Lys Val Val Glu Ile Leu Thr Asp Met Thr Ala Arg Asp
                20                  25                  30

Leu Cys Gln Leu Leu Val Tyr Lys Ser His Cys Val Asp Asp Asn Ser
            35                  40                  45

Trp Thr Leu Val Glu His His Pro Gln Leu Gly Leu Glu Arg Cys Leu
50                  55                  60

Glu Asp His Glu Ile Val Val Gln Val Glu Ser Thr Met Pro Ser Glu
65                  70                  75                  80

Ser Lys Phe Leu Phe Arg Lys Asn Tyr Ala Lys Tyr Glu Phe Phe Lys
                85                  90                  95

Asn Pro Val Asn Phe Phe Pro Asp Gln Met Val Asn Trp Cys Gln Gln
            100                 105                 110

Ser Asn Gly Gly Gln Ala Pro Val Leu Gln Asn Phe Leu Asn Thr Ser
        115                 120                 125

Ser Cys Pro Glu Ile Gln Gly Phe Leu Gln Val Lys Glu Val Gly Arg
    130                 135                 140

Lys Ser Trp Lys Lys Leu Tyr Val Cys Leu Arg Arg Ser Gly Leu Tyr
145                 150                 155                 160

Tyr Ser Thr Lys Gly Thr Ser Lys Glu Pro Arg His Leu Gln Leu Leu
                165                 170                 175

Ala Asp Leu Glu Glu Ser Ser Ile Phe Tyr Leu Ile Ala Gly Lys Lys
            180                 185                 190
```

```
Gln Tyr Asn Ala Pro Asn Glu His Gly Met Cys Ile Lys Pro Asn Lys
        195                 200                 205

Ala Lys Thr Glu Met Lys Glu Leu Arg Leu Leu Cys Ala Glu Asp Glu
210                 215                 220

Gln Ile Arg Thr Cys Trp Met Thr Ala Phe Arg Leu Leu Lys Tyr Gly
225                 230                 235                 240

Met Leu Leu Tyr Gln Asn Tyr Arg Ile Pro Gln Arg Lys Gly Leu Pro
            245                 250                 255

Pro Pro Phe Asn Ala Pro Met Arg Ser Val Ser Glu Asn Ser Leu Val
            260                 265                 270

Ala Met Asp Phe Ser Gly Gln Ile Gly Arg Val Ile Asp Asn Pro Ala
        275                 280                 285

Glu Ala Gln Ser Ala Ala Leu Glu Glu Gly His Ala Trp Arg Asn Gly
290                 295                 300

Ser Thr Arg Met Asn Ile Leu Ser Ser Gln Ser Pro Leu His Pro Ser
305                 310                 315                 320

Thr Leu Asn Ala Val Ile
                325
```

(2) INFORMATION FOR SEQ ID NO: 3:

(i) SEQUENCE CHARACTERISTICS:
        (A) LENGTH:        348 amino acids
        (B) TYPE:          amino acid
        (C) STRANDEDNESS:   single
        (D) TOPOLOGY:      linear (ii) MOLECULE TYPE:      protein (ix) FEATURE:
        (D) OTHER INFORMATION:   BLM domain of F10E9.6

(xi) SEQUENCE DESCRIPTION: SEQ ID NO: 3:

```
Lys Glu Ala Lys Val Thr Lys Ile Phe Val Lys Phe Val Glu Asp
1               5                   10                  15

Gly Glu Ala Leu Gln Leu Leu Ile Asp Glu Arg Trp Thr Val Ala Asp
            20                  25                  30

Thr Leu Lys Gln Leu Ala Glu Lys Asn His Ile Ala Leu Met Glu Asp
        35                  40                  45

His Cys Ile Val Glu Glu Tyr Pro Glu Leu Tyr Ile Lys Arg Val Tyr
    50                  55                  60

Glu Asp His Glu Lys Val Val Glu Asn Ile Gln Met Trp Val Gln Asp
65                  70                  75                  80

Ser Pro Asn Lys Leu Tyr Phe Met Arg Arg Pro Asp Lys Tyr Ala Phe
            85                  90                  95

Ile Ser Arg Pro Glu Leu Tyr Leu Leu Thr Pro Lys Thr Ser Asp His
            100                 105                 110

Met Glu Ile Pro Ser Gly Asp Gln Trp Thr Ile Asp Val Lys Gln Lys
        115                 120                 125

Phe Val Ser Glu Tyr Phe His Arg Glu Pro Val Val Pro Pro Glu Met
            130                 135                 140

Glu Gly Phe Leu Tyr Leu Lys Ser Asp Gly Arg Lys Ser Trp Lys Lys
145                 150                 155                 160

His Tyr Phe Val Leu Arg Pro Ser Gly Leu Tyr Tyr Ala Pro Lys Ser
                165                 170                 175

Lys Lys Pro Thr Thr Lys Asp Leu Thr Cys Leu Met Asn Leu His Ser
            180                 185                 190
```

```
Asn Gln Val Tyr Thr Gly Ile Gly Trp Glu Lys Lys Tyr Lys Ser Pro
        195                 200                 205

Thr Pro Trp Cys Ile Ser Ile Lys Leu Thr Ala Leu Gln Met Lys Arg
    210                 215                 220

Ser Gln Phe Ile Lys Tyr Ile Cys Ala Glu Asp Glu Met Thr Phe Lys
225                 230                 235                 240

Lys Trp Leu Val Ala Leu Arg Ile Ala Lys Asn Gly Ala Glu Leu Leu
                245                 250                 255

Glu Asn Tyr Glu Arg Ala Cys Gln Ile Arg Arg Glu Thr Leu Gly Pro
                260                 265                 270

Ala Ser Ser Met Ser Ala Ala Ser Ser Thr Ala Ile Ser Glu Val
                275                 280                 285

Pro His Ser Leu Ser His His Gln Arg Thr Pro Ser Val Ala Ser Ser
    290                 295                 300

Ile Gln Leu Ser Ser His Met Met Asn Asn Pro Thr His Pro Leu Ser
305                 310                 315                 320

Val Asn Val Arg Asn Gln Ser Pro Ala Ser Phe Ser Val Asn Ser Cys
                325                 330                 335

Gln Gln Ser His Pro Ser Arg Thr Ser Ala Lys Leu
                340                 345
```

(2) INFORMATION FOR SEQ ID NO: 4:

(i) SEQUENCE CHARACTERISTICS:
        (A) LENGTH:         101 amino acids
        (B) TYPE:           amino acid
        (C) STRANDEDNESS:   single
        (D) TOPOLOGY:      linear (ii) MOLECULE TYPE:       protein (ix) FEATURE:
        (D) OTHER INFORMATION:   Consensus (xi) SEQUENCE DESCRIPTION: SEQ ID NO: 4:

```
Glu Val Lys Phe Glu Asp Gly Val Ile Thr Leu Lys His Leu Val Glu
1               5                   10                  15

Pro Leu Leu Arg Glu Asp His Glu Val Val Phe Phe Lys Lys Tyr Phe
                20                  25                  30

Pro Leu Phe Leu Gln Phe Leu Pro Glu Gly Phe Leu Leu Lys Gly Arg
            35                  40                  45

Ser Trp Lys Lys Tyr Leu Arg Ser Gly Leu Tyr Tyr Lys Arg Leu Leu
        50                  55                  60

Leu Val Tyr Lys Tyr Pro Ile Lys Leu Leu Cys Glu Asp Glu Trp Ala
65                  70                  75                  80

Phe Arg Leu Lys Gly Leu Asn Tyr Arg Ser Val Phe Ser Asn Pro Ser
                85                  90                  95

Arg Leu Ser Ala Ile
            100
```

(2) INFORMATION FOR SEQ ID NO: 5:

(i) SEQUENCE CHARACTERISTICS:
        (A) LENGTH:         534 amino acids
        (B) TYPE:           amino acid
        (C) STRANDEDNESS:   single
        (D) TOPOLOGY:      linear (ii) MOLECULE TYPE:       protein (ix) FEATURE:

(D) OTHER INFORMATION: GRB-7

(xi) SEQUENCE DESCRIPTION: SEQ ID NO: 5:

```
Glu Leu Asp Leu Ser Pro Thr His Leu Ser Ser Pro Glu Asp Val
 1               5                  10                  15

Cys Pro Thr Pro Ala Thr Pro Pro Glu Thr Pro Pro Pro Asp Asn
                20                  25                  30

Pro Pro Pro Gly Asp Val Lys Arg Ser Gln Pro Leu Pro Ile Pro Ser
                35                  40                  45

Ser Arg Lys Leu Arg Glu Glu Glu Phe Gln Ala Thr Ser Leu Pro Ser
 50                  55                      60

Ile Pro Asn Pro Phe Pro Glu Leu Cys Ser Pro Ser Gln Lys Pro
 65                  70                  75                  80

Ile Leu Gly Gly Ser Ser Gly Ala Arg Gly Leu Leu Pro Arg Asp Ser
                85                  90                  95

Ser Arg Leu Cys Val Val Lys Val Tyr Ser Glu Asp Gly Ala Cys Arg
                100                 105                 110

Ser Val Glu Val Ala Ala Gly Ala Thr Ala Arg His Val Cys Glu Met
                115                 120                 125

Leu Val Gln Arg Ala His Ala Leu Ser Asp Glu Ser Trp Gly Leu Val
 130                 135                     140

Glu Ser His Pro Tyr Leu Ala Leu Glu Arg Gly Leu Glu Asp His Glu
145                  150                 155                 160

Phe Val Val Glu Val Gln Glu Ala Trp Pro Val Gly Gly Asp Ser Arg
                165                 170                 175

Phe Ile Phe Arg Lys Asn Phe Ala Lys Tyr Glu Leu Phe Lys Ser Pro
                180                 185                 190

Pro His Thr Leu Phe Pro Glu Lys Met Val Ser Ser Cys Leu Asp Ala
    195                 200                 205

Gln Thr Gly Ile Ser His Glu Asp Leu Ile Gln Asn Phe Leu Asn Ala
 210                 215                     220

Gly Ser Phe Pro Glu Ile Gln Gly Phe Leu Gln Leu Arg Gly Ser Gly
225                  230                 235                 240

Arg Gly Ser Gly Arg Lys Leu Trp Lys Arg Phe Cys Phe Leu Arg
                245                 250                 255

Arg Ser Gly Leu Tyr Tyr Ser Thr Lys Gly Thr Ser Lys Asp Pro Arg
                260                 265                 270

His Leu Gln Tyr Val Ala Asp Val Asn Glu Ser Asn Val Tyr Val Val
    275                 280                 285

Thr Gln Gly Arg Lys Leu Tyr Gly Met Pro Thr Asp Phe Gly Phe Cys
 290                 295                     300

Val Lys Pro Asn Lys Leu Arg Asn Gly His Lys Gly Leu His Ile Phe
305                  310                 315                 320

Cys Ser Glu Asp Glu Gln Ser Arg Thr Cys Trp Leu Ala Ala Phe Arg
                325                 330                 335

Leu Phe Lys Tyr Gly Val Gln Leu Tyr Lys Asn Tyr Gln Gln Ala Gln
                340                 345                 350

Ser Arg His Leu Arg Leu Ser Tyr Leu Gly Ser Pro Pro Leu Arg Ser
    355                 360                 365

Val Ser Asp Asn Thr Leu Val Ala Met Asp Phe Ser Gly His Ala Gly
    370                 375                     380

Arg Val Ile Asp Asn Pro Arg Glu Ala Leu Ser Ala Met Glu Glu
385                  390                 395                 400
```

```
Ala Gln Ala Trp Arg Lys Lys Thr Asn His Arg Leu Ser Leu Pro Thr
                405                 410                 415

Thr Cys Ser Gly Ser Ser Leu Ser Ala Ala Ile His Arg Thr Gln Pro
                420                 425                 430

Trp Phe His Gly Arg Ile Ser Arg Glu Glu Ser Gln Arg Leu Ile Gly
                435                 440                 445

Gln Gln Gly Leu Val Asp Gly Val Phe Leu Val Arg Glu Ser Gln Arg
            450                 455                 460

Asn Pro Gln Gly Phe Val Leu Ser Leu Cys His Leu Gln Lys Val Lys
465                 470                 475                 480

His Tyr Leu Ile Leu Pro Ser Glu Asp Glu Gly Cys Leu Tyr Phe Ser
                485                 490                 495

Met Asp Glu Gly Gln Thr Arg Phe Thr Asp Leu Leu Gln Leu Val Glu
                500                 505                 510

Phe His Gln Leu Asn Arg Gly Ile Leu Pro Cys Leu Arg His Cys
                515                 520                 525

Cys Ala Arg Val Ala Leu
            530

(2) INFORMATION FOR SEQ ID NO: 6:

(i) SEQUENCE CHARACTERISTICS:
        (A) LENGTH:            618 amino acids
        (B) TYPE:              amino acid
        (C) STRANDEDNESS:      single
        (D) TOPOLOGY:          linear (ii) MOLECULE TYPE:        protein (ix) FEATURE:
        (D) OTHER INFORMATION:  GRB-10

(xi) SEQUENCE DESCRIPTION: SEQ ID NO: 6:

Asp Ile Asn Ser Ser Val Glu Ser Leu Asn Ser Ala Cys Asn Met Gln
1               5                   10                  15

Ser Asp Thr Asp Thr Ala Pro Leu Leu Glu Asp Gly Gln His Ala Ser
                20                  25                  30

Asn Gln Gly Ala Ala Ser Ser Arg Gly Gln Pro Gln Ala Ser Pro
            35                  40                  45

Arg Gln Lys Met Gln Arg Ser Gln Pro Val His Ile Leu Arg Arg Leu
        50                  55                  60

Gln Glu Glu Asp Gln Gln Leu Arg Thr Ala Ser Leu Pro Ala Ile Pro
65                  70                  75                  80

Asn Pro Phe Pro Glu Leu Thr Gly Ala Ala Pro Gly Ser Pro Pro Ser
                85                  90                  95

Val Ala Pro Ser Ser Leu Pro Pro Pro Ser Gln Pro Pro Ala Lys
                100                 105                 110

His Cys Gly Arg Cys Glu Lys Trp Ile Pro Gly Glu Asn Thr Arg Gly
                115                 120                 125

Asn Gly Lys Arg Lys Ile Trp Arg Trp Gln Phe Pro Pro Gly Phe Gln
            130                 135                 140

Leu Ser Lys Leu Thr Arg Pro Gly Leu Trp Thr Lys Thr Thr Ala Arg
145                 150                 155                 160

Phe Ser Lys Lys Gln Pro Lys Asn Gln Cys Pro Thr Asp Thr Val Asn
                165                 170                 175

Pro Val Ala Arg Met Pro Thr Ser Gln Met Glu Lys Leu Arg Leu Arg
                180                 185                 190
```

-continued

```
Lys Asp Val Lys Val Phe Ser Glu Asp Gly Thr Ser Lys Val Val Glu
            195                 200                 205

Ile Leu Thr Asp Met Thr Ala Arg Asp Leu Cys Gln Leu Leu Val Tyr
        210                 215                 220

Lys Ser His Cys Val Asp Asp Asn Ser Trp Thr Leu Val Glu His His
225                 230                 235                 240

Pro Gln Leu Gly Leu Glu Arg Cys Leu Glu Asp His Glu Ile Val Val
                245                 250                 255

Gln Val Glu Ser Thr Met Pro Ser Glu Ser Lys Phe Leu Phe Arg Lys
            260                 265                 270

Asn Tyr Ala Lys Tyr Glu Phe Phe Lys Asn Pro Val Asn Phe Phe Pro
        275                 280                 285

Asp Gln Met Val Asn Trp Cys Gln Gln Ser Asn Gly Gly Gln Ala Gln
290                 295                 300

Leu Leu Gln Asn Phe Leu Asn Thr Ser Ser Cys Pro Glu Ile Gln Gly
305                 310                 315                 320

Phe Leu Gln Val Lys Glu Val Gly Arg Lys Ser Trp Lys Lys Leu Tyr
                325                 330                 335

Val Cys Leu Arg Arg Ser Gly Leu Tyr Tyr Ser Thr Lys Gly Thr Ser
            340                 345                 350

Lys Glu Pro Arg His Leu Gln Leu Leu Ala Asp Leu Glu Glu Ser Ser
        355                 360                 365

Ile Phe Tyr Leu Ile Ala Gly Lys Lys Gln Tyr Asn Ala Pro Asn Glu
        370                 375                 380

His Gly Met Cys Ile Lys Pro Asn Lys Ala Lys Thr Glu Met Lys Glu
385                 390                 395                 400

Leu Arg Leu Leu Cys Ala Glu Asp Glu Gln Ile Arg Thr Cys Trp Met
                405                 410                 415

Thr Ala Phe Arg Leu Leu Lys Tyr Gly Met Leu Leu Tyr Gln Asn Tyr
            420                 425                 430

Arg Ile Pro Gln Arg Lys Gly Leu Pro Pro Phe Asn Ala Pro Met
        435                 440                 445

Arg Ser Val Ser Glu Asn Ser Leu Val Ala Met Asp Phe Ser Gly Gln
450                 455                 460

Ile Gly Arg Val Ile Asp Asn Pro Ala Glu Ala Gln Ser Ala Ala Leu
465                 470                 475                 480

Glu Glu Gly His Ala Trp Arg Asn Gly Ser Thr Arg Met Asn Ile Leu
                485                 490                 495

Ser Ser Gln Ser Pro Leu His Pro Ser Thr Leu Asn Ala Val Ile His
            500                 505                 510

Arg Thr Gln His Trp Phe His Gly Arg Ile Ser Arg Glu Glu Ser His
        515                 520                 525

Arg Ile Ile Lys Gln Gln Gly Leu Val Asp Gly Leu Phe Leu Leu Arg
        530                 535                 540

Asp Ser Gln Ser Asn Pro Lys Ala Phe Val Leu Thr Leu Cys His His
545                 550                 555                 560

Gln Lys Ile Lys Asn Phe Gln Ile Leu Pro Cys Glu Asp Asp Gly Gln
                565                 570                 575

Thr Phe Phe Thr Leu Asp Asp Gly Asn Thr Lys Phe Ser Asp Leu Ile
            580                 585                 590
```

-continued

```
Gln Leu Val Asp Phe Tyr Gln Leu Asn Lys Gly Val Leu Pro Cys Lys
        595                 600                 605

Leu Lys His His Cys Ile Arg Val Ala Leu
        610                 615
```

TREATMENT OR DIAGNOSIS OF DISEASES OR CONDITIONS ASSOCIATED WITH A BLM DOMAIN

This application is a continuation of Ser. No. 08/522,539, filed Sep. 1, 1995, now abandoned, which is a continuation of Ser. No. 08/212,234, filed Mar. 14, 1994, now abandoned.

FIELD OF THE INVENTION

The present invention relates generally to the fields of chemistry, biology, and medicine and more specifically to the diagnosis and treatment of various diseases or conditions.

BACKGROUND OF THE INVENTION

The present invention concerns methods of diagnosis and treatment of diseases or conditions characterized by abnormal cellular signal transduction. The invention is based on the observation that molecules believed to play an important role in cellular signal transduction contain a unique domain that can bind to signal transduction pathway components thereby influencing cellular events. The following is a discussion of relevant art, none of which is admitted to be prior art to the invention.

Receptor tyrosine kinases belong to a family of transmembrane proteins and have been implicated in cellular signaling pathways. The predominant biological activity of some receptor tyrosine kinases is the stimulation of cell growth and proliferation, while other receptor tyrosine kinases are involved in arresting growth and promoting differentiation. In some instances, a single tyrosine kinase can inhibit, or stimulate, cell proliferation depending on the cellular environment in which it is expressed. (Schlessinger, J. and Ullrich, A., Neuron, 9(3):383–391, 1992.)

Receptor tyrosine kinases are composed of at least three domains: an extracellular ligand binding domain, a transmembrane domain and a cytoplasmic catalytic domain that can phosphorylate tyrosine residues. Ligand binding to membrane-bound receptors induces the formation of receptor dimers and allosteric changes that activate the intracellular kinase domains and result in the self-phosphorylation (autophosphorylation and/or transphosphorylation) of the receptor on tyrosine residues. Individual phosphotyrosine residues of the cytoplasmic domains of receptors may serve as specific binding sites that interact with a host of cytoplasmic signalling molecules, thereby activating various signal transduction pathways (Ullrich, A. and Schlessinger, J., 1990, Cell 61:203–212).

The intracellular, cytoplasmic, non-receptor protein tyrosine kinases do not contain a hydrophobic transmembrane domain and share non-catalytic domains in addition to sharing their catalytic kinase domains. Such non-catalytic domains include the SH2 domains (SRC homology domain 2; Sadowski, I. et al., Mol. Cell. Biol. 6:4396–4408; Koch, C. A. et al., 1991, Science 252:668–674) and SH3 domains (SRC homology domain 3; Mayer, B. J. et al., 1988, Nature 332:269–272). Such non-catalytic domains are also thought to include the PH domain (Musacchio et al., 1993, TIBS 18:342–348). The noncatalytic domains are thought to be important in the regulation of protein-protein interactions during signal transduction (Pawson, T. and Gish, G., 1992, Cell 71:359–362).

A central feature of signal transduction (for reviews, see Posada, J. and Cooper, J. A., 1992, Mol. Biol. Cell 3:583–392; Hardie, D.G., 1990, Symp. Soc. Exp. Biol. 44:241–255), is the reversible phosphorylation of certain proteins. Receptor phosphorylation stimulates a physical association of the activated receptor with target molecules. Some of the target molecules are in turn phosphorylated. Such phosphorylation transmits a signal to the cytoplasm. Other target molecules are not phosphorylated, but assist in signal transmission by acting as adapter molecules for secondary signal transducer proteins. For example, receptor phosphorylation and the subsequent allosteric changes in the receptor recruit the Grb-2/SOS complex to the catalytic domain of the receptor where its proximity to the membrane allows it to activate ras Pawson, T. and Schiessinger, J., Current Biol. 13:434, 1993.

The secondary signal transducer molecules generated by activated receptors result in a signal cascade that regulates cell functions such as cell division or differentiation. Reviews describing intracellular signal transduction include Aaronson, S. A., Science, 254:1146–1153, 1991; Schlessinger, J. Trends Biochem. Sci., 13:443–447, 1988; and Ullrich, A., and Schlessinger, J., Cell, 61:203–212, 1990.

Abnormalities in signal transduction pathways can lead to various diseases in at least three different ways: (1) underactivity (2) mutation, and (3) overexpression. An example of underactivity is observed in some forms of diabetes. Examples of mutation include the role of BCR-ABL in chronic myelogenous leukemia and acute lymphocytic leukemia. Pendergrast et al., 1993, Cell 75:175–185.

Overexpression of certain protein tyrosine kinases has been shown to subvert normal growth control pathways and lead to oncogenesis (reviewed in Hunter, T., 1991, Cell 64:249–270). An example of a protein that may participate in the aberrant growth of breast cancer cells is HER2, also known as c-erbB-2 (Coussens et al. , 1985 Science 230:1132–1139; Yamamoto et al., 1986, Nature, 319:521–527). This receptor was also isolated as the rat oncogene neu, an oncogene responsible for chemically induced rat glioblastomas (Padhy et al., 1982 Cell, 28:865–871; Schechter et al., 1984 Nature 312:513–516; Bargmann et al., 1986, Nature, 319:226–230). HER2/erbB-2 is known to be amplified and overexpressed in about 25% of human breast cancers (Slamon et al., 1987 Science 235:177–182; Slamon et al., 1989 Science 244:707–712).

SUMMARY OF THE INVENTION

This invention relates to methods for treatment of a disease or condition in organisms, or for diagnosis of such diseases or conditions involved in abnormal protein-protein interactions.

A newly identified region, herein termed the BLM region or domain, has been determined to be involved in a protein-protein interaction. This interaction is associated with the basic signalling function of proteins associated with various diseases or conditions. Such diseases or conditions include cell adhesion diseases, neuronal diseases, oncogenic disorders, diseases associated with defects in cellular movement or in developmental processes. For example, specific diseases or conditions include breast cancer, atherosclerosis, inflammation, and diseases associated with inappropriate activities of platelets, mononuclear, or neutrophil cells.

Measurement of the level of interaction of the BLM domain with its natural binding partner has been determined to be a useful measure of the existence of certain diseases or conditions. Such diseases or conditions are thus characterized by inappropriate interaction of the BLM domain with its natural binding partner. Diseases or conditions characterized by abnormal levels of interaction between the BLM domain and its natural binding partner can be alleviated to some extent by disrupting or promoting that interaction in vivo. In addition, useful agents for treatment of such diseases can be identified by standard screening protocols in which measurement of such interaction is determined. For example, such an agent may be a peptide which either comprises, consists of, or consists essentially of the BLM domain.

Thus, in a first aspect the invention features a method for treatment of a disease or condition in an organism characterized by an abnormal level of interaction between a BLM domain and its natural binding partner. The disease or condition may also be characterized by an abnormality in a signal transduction pathway, wherein the pathway contains a protein with a BLM domain. The method includes disrupting or promoting that interaction (or signal) in vivo. The method also involves inhibiting the activity of the complex formed between the BIM domain-containing protein and its natural binding partner.

In a related aspect the invention features a method for diagnosis of such a disease or condition by detecting the level of such interaction as an indication of that disease or condition. The diagnosis may also involve the detection of an abnormal amount or intensity of a signal generated by a signal transduction pathway, wherein the signal transduction pathway contains a protein having a BLM domain.

In yet another related aspect the invention features a method for screening for an agent useful for treatment of such a disease or condition by assaying potential agents for the ability to disrupt or promote that interaction. The screening may also involve assaying potential agents for the ability to remove or reduce an abnormality in a signal transduction pathway, wherein the signal transduction pathway contains a protein with a BLM domain.

The invention also features a peptide comprising, consisting or consisting essentially of a BIM domain. By "comprising" is meant including, but not limited to, whatever follows the word "comprising". Thus, use of the term "comprising" indicates that the listed elements are required or mandatory, but that other elements are optional and may or may not be present. By "consisting of" is meant including, and limited to, whatever follows the phrase "consisting of". Thus, the phrase "consisting of" indicates that the listed elements are required or mandatory, and that no other elements may be present. By "consisting essentially of" is meant including any elements listed after the phrase, and limited to other elements that do not interfere with or contribute to the activity or action specified in the disclosure for the listed elements. Thus, the phrase "consisting essentially of" indicates that the listed elements are required or mandatory, but that other elements are optional and may or may not be present depending upon whether or not they affect the activity or action of the listed elements.

In preferred embodiments, the disease or condition which is diagnosed or treated are those described above, and the agent is a dominant negative mutant protein provided by gene therapy or other equivalent methods as described below. That is, the agent is a peptide which blocks interaction of the BLM domain with its natural binding partner. The peptide may be recombinant, purified, or placed in a pharmaceutically acceptable carrier or diluent. The peptide may be used to produce antibodies and may either contain or be complementary to at least 20 amino acids from the BLM domain. In the screening method, transformed animals, e.g., mice containing proteins having a BLM domain, for example, the GRB-7 or GRB-10 protein, or the F10E9.6 protein (see below) may be used.

By "dominant negative mutant protein" is meant a mutant protein that interferes with the normal signal transduction pathway. The dominant negative mutant protein contains the domain of interest (e.g., the BLM domain), but has a mutation preventing proper signalling, for example by preventing binding of a second domain from the same protein. One example of a dominant negative protein is described in Millaur, B. et al., *Nature* Feb. 10, 1994.

In yet other preferred embodiments, the specific region is that corresponding to the BLM domain in GRB-7 (SEQ ID NO:1) (as shown in the figures) between bases encoding amino acids 95 to 428 and, in particular, those bases 5' of the pleckstrin domain, i.e., between bases encoding amino acids 95 and 231.

By "disease or condition" is meant a state in an organism, e.g., a human, which is recognized as abnormal by members of the medical community.

The disease or condition may be characterized by an abnormality in one or more signal transduction pathways in a cell, wherein one of the components of the signal transduction pathway is a protein containing a BLM domain. An abnormal level is that level which is statistically different from the level observed in organisms not suffering from such a disease or condition and may be characterized as either an excess amount or intensity of signal or a deficient amount or intensity of signal. The abnormality in signal transduction may be realized as an abnormality in cell growth, migration or other function.

The disease or condition may also be characterized by an abnormal level of interaction between a BLM domain and its natural binding partner. An abnormal interaction level may also either be greater or less than the normal level and may impair the normal performance or function of the organism.

The disease or condition may be characterized by an abnormality in the signal transduction pathway even if the level of interaction between the BLM domain and its natural binding partner is normal. However, since the interaction between the BLM domain and its natural binding partner is part of the signal transduction pathway, it is still possible to treat such a disease by interfering with the level of interaction between the BLM domain and its natural binding partner.

Thus, it is also possible to screen for agents that will be useful for treating a disease or condition, characterized by an abnormality in the signal transduction pathway, by testing compounds for their ability to affect the interaction between a BLM domain and its natural binding partner since the complex formed by such interaction is part of the signal transduction pathway.

By "disrupt" is meant that the interaction between the BLM domain and its natural binding partner is reduced either by preventing expression of a protein containing a BLM domain, or by preventing expression of its natural binding partner, or by specifically preventing interaction of the naturally synthesized proteins or by interfering with the interaction of the proteins.

By "promote" is meant that the interaction between the BLM domain and its natural binding partner is increased either by increasing expression of a protein containing a BLM domain, or by increasing expression of its natural binding partner, or by promoting interaction of the proteins.

By "diagnosis" is meant any method of identifying a symptom normally associated with a given disease or condition. Thus, an initial diagnosis may be conclusively established as correct by the use of additional confirmatory evidence such as the presence of other symptoms. Current classification of various diseases and conditions is constantly changing as more is learned about the mechanisms causing the diseases or conditions. Thus, the detection of an important symptom, such as the detection of an abnormal level of interaction between a BLM domain containing protein and it natural binding partner (or the detection of an abnormal level of signal transduction in a pathway containing a protein with a BLM domain) may form the basis to define and diagnose a newly named disease or condition. For example, conventional cancers are classified according to the location of the tumor, i.e, breast cancer, ovarian cancer, etc. However, a subset of these cancers are both associated with the overexpression of Her2, and as the role of Her2 becomes more fully understood, these cancers may be reclassified as Her2 cancers regardless of the location of the tumor.

By "organism" is meant any living creature. The term includes mammals, and specifically humans. By "screening" is meant investigating organisms for the presence or absence of a property. The process includes measuring and detecting various properties, including the level of signal transduction and the level of interaction between a protein having a BLM domain and its natural binding partner.

By "interact" is meant any physical association between proteins, whether covalent or non-covalent. Examples of non-covalent bonds include electrostatic bonds, hydrogen bonds, and Van der Waals bonds. Stryer, Biochemistry, 1988, pages 7–8. Furthermore, the interactions between proteins may either be direct or indirect. Thus, the association between two given proteins may be achieved with an intermediary agent, or several such agents, that connects the two proteins of interest. Another example of an indirect interaction is the independent production, stimulation, or inhibition of both a BLM domain and its natural binding partner by a regulatory agent. (Schlessinger, 1992, Neuron 9:383–391) Depending upon the type of interaction present, various methods may be used to measure the level of interaction. For example, the strengths of covalent bonds are often measured in terms of the energy required to break a certain number of bonds (i.e., kcal/mol) Non-covalent interactions are often described as above and also in terms of the distance between the interacting molecules. Indirect interactions may be described in a number of ways, including the number of intermediary agents involved, or the degree of control exercised over the BLM domain relative to the control exercised over its natural binding partner.

By "natural binding partner" is meant a protein that interacts with a BLM domain. Given that the PH domain is a subdomain of the present BLM domain, it is possible that some or all of the natural binding partners for the PH domain may also serve as natural binding partners for the BLM domain. In addition, a natural binding partner for a BLM domain may only interact with the BLM domain and not the PH domain.

The structure (primary, secondary, or tertiary) of the particular natural binding partner will influence the particular type of interaction between the BLM domain and the natural binding partner. For example, if the natural binding partner comprises a sequence of amino acids complementary to the BLM domain, covalent bonding may be a possible interaction. Similarly, other structural characteristics may allow for other corresponding interactions. The interaction is not limited to particular residues and specifically may involve phosphotyrosine, phosphoserine, or phosphothreonine residues.

A broad range of sequences may be capable of interacting with BLM domain. Experience with another signalling domain, the SH2 domain, has demonstrated that the range of sequences that binds that given domain may be much broader than was initially expected. Fry et al, Protein Science, 1993, 2:1785–1797. Therefore, using techniques well known in the art, one may identify several natural binding partners for the BLM domain.

By "signal transduction pathway" is meant the sequence of events that involves the transmission of a message from an extracellular protein to the cytoplasm through a cell membrane. The signal ultimately will cause the cell to perform a particular function, for example, to proliferate and therefore cause cancer. Various mechanisms for the signal transduction pathway (Fry et al., 1993, Protein Science, 2:1785–1797) provide possible methods for measuring the amount or intensity of a given signal. Depending upon the particular disease associated with the abnormality in a signal transduction pathway, various symptoms may be detected. For example, if the disease is breast cancer, one may detect cell proliferation or tumor size, among other symptoms. Those skilled in the art recognize those symptoms that are associated with the various other diseases described herein. Furthermore, since some adaptor molecules recruit secondary signal transducer proteins towards the membrane, one measure of signal transduction is the concentration and localization of various proteins and complexes. In addition, conformational changes that are involved in the transmission of a signal may be observed using circular dichroism and fluorescence studies.

One signal transduction pathway that has been studied is the Ras signalling pathway. (Pendergrast et al., 1993, Cell 75:175–185) The role of the GRB2 protein in the Ras signalling pathway (and the interaction with BCR-ABL, an oncoprotein implicated in certain human leukemias) was elucidated using a combination of biochemical and genetic studies. Similar studies are expected to elucidate the specific signalling pathway(s) affected by BLM domain containing proteins such as Grb7.

Other features and advantages of the invention will be apparent from the following description of the preferred embodiments thereof, and from the claims.

DESCRIPTION OF THE PREFERRED EMBODIMENTS

The drawings will first briefly be described.
Drawings
FIG. 1 is a diagrammatic representation of the BLM domain shown as regions of identity in the GRB-10, GRB-7, and F10E9.6 proteins at the amino acid level;

FIG. 2 is an alignment of the BLM domain of GRB-7 (SEQ ID NO:1), GRB-10 (SEQ ID NO:2), F10E9.6 (SEQ ID NO:3) and within that the pleckstrin domain and also showing the consensus sequence (SEQ ID NO:4);

FIG. 3 is the amino acid sequence of GRB-7 (SEQ ID NO:5) compared to GRB-10 (SEQ ID NO:6) showing the BLM domain;

Figure 5:
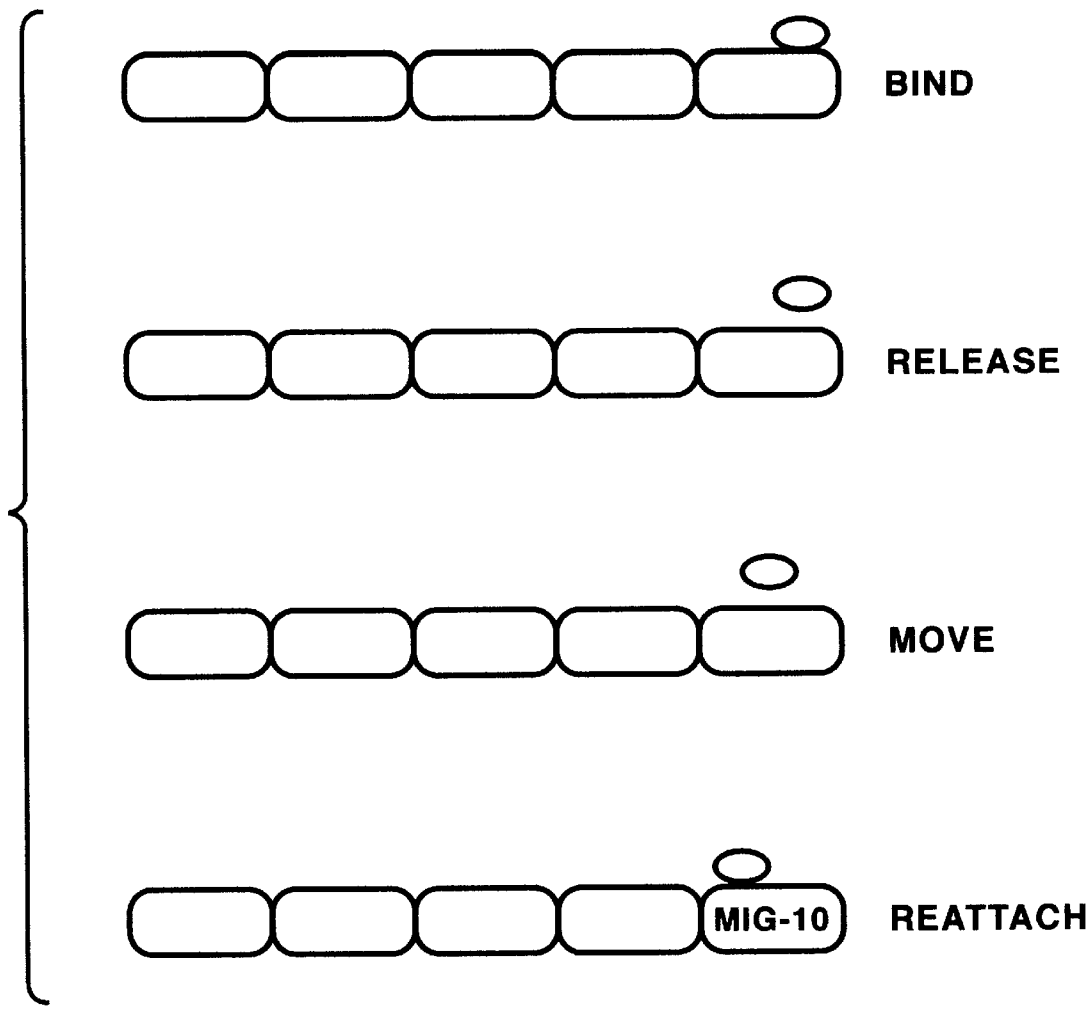

FIG. 5 is a diagrammatic representation of the association between a stationary cell and a cell which is moving.
The BLM Domain Referring to FIG. 1, examples of the BLM domain are shown diagrammatically in three newly characterized proteins. The region shown corresponds to amino acids between about 200 and 500 in the noted proteins, and includes the plextrin domain defined by Musacchio et al., 18 *TIBS*

September 1993 (and references cited therein). (The term "pleckstrin domain or PH domain" is used in this application as defined by Musacchio et al.) Those in the art will recognize that BLM equivalent domains are readily identified as those having at least 20% identity in the amino acid sequence in the noted regions or perform the same function despite a lower percentage of identity. The percentage of identity between two domains is calculated by dividing the number of amino acids that are the same in a given region by the total number of amino acids in the given region. Proteins including such domains are readily identified using standard protocols.

Other proteins with BLM equivalent domains may be identified as those having at least 30% similarity or perform the same function despite having an even lower percentage of similarity. The percentage of similarity is calculated using a computer program (such as the GCG Bestfit program) that scores a protein based upon the number of gaps that must be induced to achieve similarity.

Regions that have at least 20% identity or 30% similarity are recognized as containing the same domain independent of any knowledge of the function of the proteins or domains. However, when knowledge regarding the function of the proteins or domain is known, then equivalent domains may be identified with much lower identity or similarity. For example, the pleckstrin domain contains two proteins that only share approximately 5% identity to each other. Musacchio, id.

Figure 1:
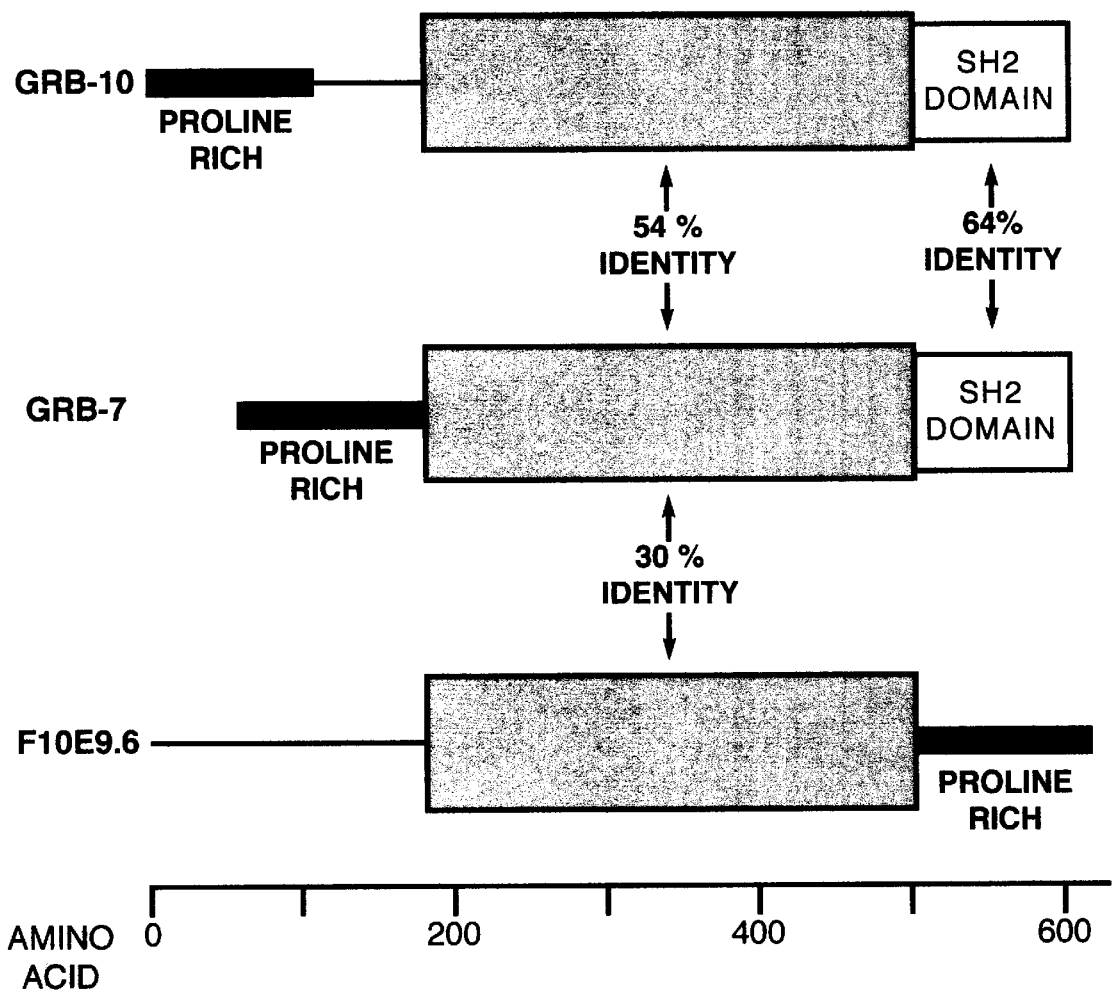

Referring to FIG. 2, the amino acid sequence of the three proteins, shown in FIG. 1, are provided with the consensus sequence. The standard single letter amino acid code is used in the figure. The BLM domain is that shown in GRB-7 (SEQ ID NO:1) between amino acids 95 and 428, and the 5' region of the BLM domain is that between amino acids 95 and 231. Thus, the 5' region is 5' of the pleckstrin domain.

Referring to FIG. 3, the protein sequence of GRB-7 (SEQ ID NO:5) and GRB-10 (SEQ ID NO:6) is shown, demonstrating the high degree of conservation in the BLM domain and pleckstrin domain.

BLM Domain Interaction

Figure 4:
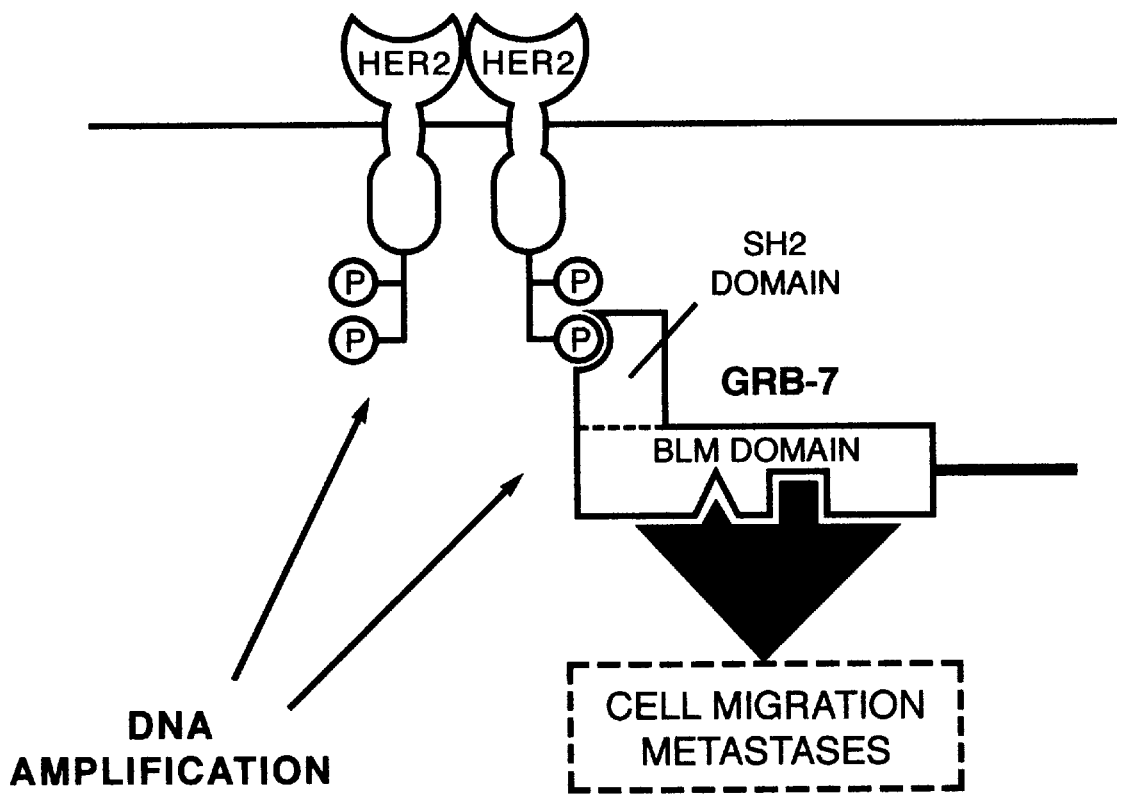
FIG. 4 is a diagrammatic representation of a proposed Her-2; GRB-7; and natural binding partner signalling process in breast cancer.

Referring to FIG. 4, the present invention is based upon the interaction of the BLM domain of proteins such as GRB-7 with a natural binding partner (shown as a shaded triangle in the lower portion of the Figure).

Specifically, FIG. 4 shows the interaction of Her-2 with GRB-7 in the SH2 domain. See, Stein et al., 13 *EMBO Journal*, 1994 (Appendix A, including figures). This invention is designed to measure and/or to affect this interaction between GRB-7, or an equivalent BLM domain from this or another protein, and the natural binding partner of that domain. By such control of the interaction of the BLM domain with its natural binding partner, diseases associated with problems in cell migration and metastases can be diagnosed and treated.

For example, referring to FIG. 5 there is shown a diagrammatic representation of the role of the interaction between the BLM domain and its natural binding partner in movement of cells. Specifically, a mobile cell binds another cell. Without being bound to any particular theory of the invention, it is presently believed that the interaction between the BLM domain and its natural ligand may be involved in the signal transduction pathway that controls the affinity of cell receptors, cell adhesion, and cell migration.

GRB-7

Isolation of the GRB-7 gene is described in Margolis et al., (U.S. patent application Ser. No. 07/906,349, filed Jun. 30, 1992) hereby incorporated by reference.

GRB-10 gene

GRB-10 was cloned from λEXlox NIH 3T3 (mouse fibroblast cell line) using the CORT technique. The probe was the EGF-Receptor carboxyterminus and the methodology the same as described for the other GRB's (Skolnik et al. 65 *Cell* 83–90, 1991; Lowenstein et al., 70 *Cell* 431, 1992; Margolis et al., *PNAS*, 89:8894, 1992. The randomly primed NIH 3T3 library was generated in our laboratory using standard techniques (Sambrook et al., Molecular Cloning. A Laboratory Manual, Cold Spring Harbor Laboratory Press, Cold Spring Harbor, 1989). After the initial clone was isolated, GRB-10 cDNA encoding the full length GRB-10 protein was cloned from the same library using DNA hybridization as described (Margolis et al., 3 *Cell Growth & Differ.*, 73, 1992; Margolis et al., 89 *Proc. Natl. Acad. Sci. USA* 8894, 1992).

F10E9.6

This gene corresponds to that described by Manser and Wood as the mig-10 gene. Manser and Wood, 11 *Developmental Genetics* 49, 1990, hereby incorporated by reference herein.

The present invention relates to compositions and methods for the prevention, prognostic evaluation, and treatment of oncogenic and other disorders, especially breast cancer, wherein a protein having a BLM domain is capable of complexing with its natural binding partner and is involved in such a disorder.

Specifically, the present invention relates to compositions and methods for decreasing or inhibiting the interaction between the components of the two proteins and/or decreasing or inhibiting the activity of such complexes, and to methods for identifying useful agents for such compositions. The present invention also relates to removing or reducing an abnormality in a signal transduction pathway, wherein the signal transduction pathway contains a protein with a BLM domain. Further, the present invention relates to the use of such methods and compositions for the treatment of the oncogenic disorders of interest, especially breast cancer. The present invention also relates to compositions and methods for the treatment of disorders which involve modulating the activity and/or level of individual components of the proteins, and relates to methods for the identification of agents for such treatments. Additionally, the present invention relates to methods and compositions for prognostic evaluation of such disorders. Several abbreviations, defined below, are used to describe the present invention.

| ABBREVIATIONS | | |
|---|---|---|
| Amino Acid | One Letter code | Three Letter Code |
| Alanine | A | Ala |
| Arginine | R | Arg |
| Asparagine | N | Asn |
| Aspartic Acid | D | Asp |
| Cysteine | C | Cys |
| Glutamic Acid | E | Glu |
| Glutamine | Q | Gln |
| Glycine | G | Gly |
| Histidine | H | His |
| Isoleucine | I | Ile |
| Leucine | L | Leu |
| Lysine | K | Lys |
| Methionine | M | Met |
| Phenylalanine | F | Phe |
| Proline | P | Pro |
| Serine | S | Ser |
| Threonine | T | Thr |

-continued

| ABBREVIATIONS | | |
|---|---|---|
| Amino Acid | One Letter code | Three Letter Code |
| Tryptophan | W | Trp |
| Tyrosine | Y | Tyr |
| Valine | V | Val |
| Not specified | X | |

Described herein are compositions and methods for the prevention, prognostic evaluation, and treatment of disorders, especially breast cancer, in which a protein, e.g., a protein having a BLM domain is involved.

First, methods and compositions for the treatment of such disorders are described. Such methods and compositions may include, but are not limited to the agents capable of decreasing or inhibiting the interaction between the BLM domain of the protein and its natural binding ligand and agents capable of inhibiting or decreasing the activity of such complexes, agents capable of modulating the activity and/or level of individual components of the proteins, and the use and administration of such agents.

Second, methods are described for the identification of such agents. These methods may include, for example, assays to identify agents capable of disrupting or inhibiting the interaction between components of the above described complexes, and may also include paradigms and strategies for the rational design of drugs capable of disruption and/or inhibition of such complexes.

Additionally, methods and compositions are discussed for the prognostic evaluation of disorders which involve a protein having a BLM domain.

BLM Domain Containing Proteins Natural Binding Ligand Complexes

The complexes involved in the invention include at least one member of the BLM domain-containing family of proteins, and/or a derivative thereof, and at least one member of a natural binding ligand containing protein or a derivative thereof, as described below. Under standard physiological conditions, the components of such complexes are capable of forming stable, non-covalent attachments with one or more of the other complex components. Methods for the purification and production of such protein complexes, and of cells that exhibit such complexes are described below.

Disruption of Protein Complexes

Disruption of BLM domain-containing associated protein complexes, for example by decreasing or inhibiting the interactions between component members such a complex may have differing modulatory effects on the event involved, depending on the individual protein complex.

"Disruption", as used here, is meant to refer not only to a physical separation of protein complex components, but also refers to a perturbation of the activity of the complexes, regardless of whether or not such complexes remain able, physically, to form.

"Activity", as used here, refers to the function of the protein complex in the signal transduction cascade of the cell in which such a complex is formed, i.e., refers to the function of the complex in effecting or inhibiting a transduction of an extracellular signal into a cell. For example, the effect of complex disruption may augment, reduce, or block a signal normally transduced into the cell. Likewise, depending on the disorder involved, either augmentation, reduction, or blockage of a signal normally transduced into the cell will be desirable for the treatment of the disorder.

A disorder involving a complex may, for example, develop because the presence of such a complex brings about the aberrant inhibition of a normal signal transduction event. In such a case, the disruption of the complex would allow the restoration of the usual signal transduction event. Further, an aberrant complex may bring about an altered subcellular adaptor protein localization, which may result in, for example, dysfunctional cellular events. An inhibition of the complex in this case would allow for restoration or maintenance of a normal cellular architecture. Still further, an agent or agents that cause(s) disruption of the complex may bring about the disruption of the interactions among other potential components of a complex.

Nucleotide sequences encoding peptide agents which are to be utilized intracellularly may be expressed in the cells of interest, using techniques which are well known to those of ordinary skill in the art. For example, expression vectors derived from viruses such as retroviruses, vaccinia virus, adenoviruses, adeno-associated virus, herpes viruses, or bovine papilloma virus, may be used for delivery and expression of such nucleotide sequences into the targeted cell population. Methods for the construction of such vectors are well known. See, for example, the techniques described in Maniatis et al., 1989, Molecular Cloning A Laboratory Manual, Cold Spring Harbor Laboratory, N.Y. and Ausubel et al., 1989, Current Protocols in Molecular Biology, Greene Publishing Associates and Wiley Interscience, N.Y. Complex-binding domains can be identified using, for example, techniques such as those described in Rotin et al. (Rotin, D. et al., EMBO J. 11:559–567), Songyang et al. (Songyang, S. et al., 1993, Cell 72:767–778), Felder, S. et al., 1993, Mol. Cell. Biol. 13:1449–1455, Fantl, W. J. et al., 1992, Cell 69:413–422, and Domchek, S. M. et al., 1992, Biochemistry 31:9865–9870.

Alternatively, antibodies capable of interfering with complex formation may be produced as described below and administered for the treatment of disorders involving a component capable of forming a complex with another protein. For example, neutralizing antibodies which are capable of interfering with ligand binding may be administered using standard techniques. Alternatively, nucleotide sequences encoding single-chain antibodies may be expressed within the target cell population by utilizing, for example, techniques such as those described in Marasco et al. (Marasco, W. et al., 1993, Proc. Natl. Acad. Sci. USA 90:7889–7893).

Agents which act intracellularly to interfere with the formation and/or activity of the protein complexes of the invention may also be small organic or inorganic compounds. A method for identifying these and other intracellular agents is described below.

Antibodies to Complexes

Described herein are methods for the production of antibodies which are capable of specifically recognizing a complex or an epitope thereof, or of specifically recognizing an epitope on either of the components of the complex, especially those epitopes which would not be recognized by the antibody when the component is present separate and apart from the complex. Such antibodies may include, but are not limited to polyclonal antibodies, monoclonal antibodies (mAbs), humanized or chimeric antibodies, single chain antibodies, Fab fragments, F(ab')$_2$ fragments, fragments produced by a FAb expression library, anti-idiotypic (anti-Id) antibodies, and epitope-binding fragments of any of the above. Such antibodies may be used, for example, in the detection of a complex in a biological sample, or, alternatively, as a method for the inhibition of a complex formation, thus, inhibiting the development of a disorder.

Polyclonal antibodies are heterogeneous populations of antibody molecules derived from the sera of animals immunized with an antigen, such as a complex, or an antigenic functional derivative thereof. For the production of polyclonal antibodies, various host animals may be immunized by injection with the complex including but not limited to rabbits, mice, rats, etc. Various adjuvants may be used to increase the immunological response, depending on the host species, including but not limited to Freund's (complete and incomplete), mineral gels such as lysolecithin, pluronic polyols, polyanions, peptides, oil emulsions, keyhole limpet hemocyanin, dinitrophenol, and potentially useful human adjuvants such as BCG (bacille Calmette-Guerin) and *Corynebacterium parvum.*

A monoclonal antibody, which is a substantially homogeneous population of antibodies to a particular antigen, may be obtained by any technique which provides for the production of antibody molecules by continuous cell lines in culture. These include, but are not limited to the hybridoma technique of Kohler and Milstein, (Nature 256:495–497 (1975) and U.S. Pat. No. 4,376,110), the human B-cell hybridoma technique (Kosbor et al., 1983, Immunology Today 4:72; Cole et al., 1983 Proc. Natl. Acad. Sci. USA 80:2026–2030), and the EBV-hybridoma technique (Cole et al., 1985, Monoclonal Antibodies And Cancer Therapy, Alan R. Liss, Inc., pp. 77–96). Such antibodies may be of any immunoglobulin class including IgG, IgM, IgE, IgA, IgD and any subclass thereof. The hybridoma producing the mAb of this invention may be cultivated in vitro or in vivo. Production of high titers of mAbs in vivo makes this the presently preferred method of production.

In addition, techniques developed for the production of "chimeric antibodies" (Morrison et al., 1984, Proc. Natl. Acad. Sci., 81:6851–6855; Neuberger et al., 1984, Nature, 312:604–608; Takeda et al., 1985, Nature, 314:452–454) by splicing the genes from a mouse antibody molecule of appropriate antigen specificity together with genes from a human antibody molecule of appropriate biological activity can be used. A chimeric antibody is a molecule in which different portions are derived from different animal species, such as those having a variable region derived from a murine mAb and a human immunoglobulin constant region.

Alternatively, techniques described for the production of single chain antibodies (U.S. Pat. No. 4,946,778; Bird, 1988, Science 242:423–426; Huston et al., 1988, Proc. Natl. Acad. Sci. USA 85:5879–5883; and Ward et al., 1989, Nature 334:544–546) can be adapted to produce complex-specific single chain antibodies. Single chain antibodies are formed by linking the heavy and light chain fragment of the Fv region via an amino acid bridge, resulting in a single chain polypeptide.

Antibody fragments which contain specific binding sites of a complex may be generated by known techniques. For example, such fragments include but are not limited to: the F(ab')$_2$ fragments which can be produced by pepsin digestion of the antibody molecule and the Fab fragments which can be generated by reducing the disulfide bridges of the F(ab')$_2$ fragments. Alternatively, Fab expression libraries may be constructed (Huse et al., 1989, Science, 246:1275–1281) to allow rapid and easy identification of monoclonal Fab fragments with the desired specificity to the PTK/adaptor complex.

One or more components of a protein complex may be present at a higher than normal cellular level (i.e., higher than the concentration known to usually be present in the cell type exhibiting the protein complex of interest) and/or may exhibit an abnormally increased level of cellular activity (i.e., greater than the activity known to usually be present in the cell type exhibiting the protein complex of interest).

For example, the gene encoding a protein complex component may begin to be overexpressed, or may be amplified (i.e., its gene copy number may be increased) in certain cells, leading to an increased number of component molecules within these cells. Additionally, a gene encoding a protein complex component may begin to express a modified protein product that exhibits a greater than normal level of activity. "Activity", here, refers to the normal cellular function of the component, either enzymatic or structural whose function may include, for example, bringing two or more cellular molecules into the appropriate proximity.

Such an increase in the cellular level and/or activity of a protein complex may lead to the development of a disorder. Treatment of such disorders may, therefore, be effectuated by the administration of agents which decrease the cellular level and/or the activity of the overexpressed and/or overactive protein complex component.

Techniques for decreasing the cellular level and/or the activity of one or more of the protein complex components of interest may include, but are not limited to antisense or ribozyme approaches, and/or gene therapy approaches, each of which is well known to those of skill in the art.

Antisense and Ribozyme Approaches

Included in the scope of the invention are oligoribonucleotides, including antisense RNA and DNA molecules and ribozymes that function to inhibit translation of one or more components of a protein complex. Anti-sense RNA and DNA molecules act to directly block the translation of mRNA by binding to targeted mRNA and preventing protein translation. With respect to antisense DNA, oligodeoxyribonucleotides derived from the translation initiation site, e.g., between –10 and +10 regions of the relevant nucleotide sequence, are preferred.

Ribozymes are enzymatic RNA molecules capable of catalyzing the specific cleavage of RNA. The mechanism of ribozyme action involves sequence specific interaction of the ribozyme molecule to complementary target RNA, followed by a endonucleolytic cleavage. Within the scope of the invention are engineered hammerhead or other motif ribozyme molecules that specifically and efficiently catalyze endonucleolytic cleavage of RNA sequences encoding protein complex components.

Specific ribozyme cleavage sites within any potential RNA target are initially identified by scanning the target molecule for ribozyme cleavage sites which include the following sequences, GUA, GUU and GUC. Once identified, short RNA sequences of between 15 and 20 ribonucleotides corresponding to the region of the target gene containing the cleavage site may be evaluated for predicted structural features, such as secondary structure, that may render the oligonucleotide sequence unsuitable. The suitability of candidate targets may also be evaluated by testing their accessibility to hybridization with complementary oligonucleotides, using ribonuclease protection assays. See, Draper PCT WO 93/23569.

Both anti-sense RNA and DNA molecules and ribozymes of the invention may be prepared by any method known in the art for the synthesis of RNA molecules. See, Draper, id. hereby incorporated by reference herein. These include techniques for chemically synthesizing oligodeoxyribonucleotides well known in the art such as for example solid phase phosphoramidite chemical synthesis. Alternatively, RNA molecules may be generated by in vitro and in vivo transcription of DNA sequences encoding the antisense RNA molecule. Such DNA sequences may be incorporated into a wide variety of vectors which incorporate suitable RNA polymerase promoters such as the T7 or SP6 polymerase promoters. Alternatively, antisense cDNA constructs that synthesize antisense RNA constitutively or inducibly, depending on the promoter used, can be introduced stably into cell lines.

Various modifications to the DNA molecules may be introduced as a means of increasing intracellular stability and half-life. Possible modifications include but are not limited to the addition of flanking sequences of ribo- or deoxy-nucleotides to the 5' and/or 3' ends of the molecule or the use of phosphorothioate or 2' O-methyl rather than phosphodiesterase linkages within the oligodeoxyribonucleotide backbone.

Gene Therapy

Target cell populations may be modified by introducing altered forms of one or more components of the protein complexes in order to modulate the activity of such complexes. For example, by reducing or inhibiting a complex component activity within target cells, an abnormal signal transduction event(s) leading to a condition may be decreased, inhibited, or reversed. Deletion or missense mutants of a component, that retain the ability to interact with other components of the protein complexes but cannot function in signal transduction may be used to inhibit an abnormal, deleterious signal transduction event.

Expression vectors derived from viruses such as retroviruses, vaccinia virus, adenovirus, adeno-associated virus, herpes viruses, or bovine papilloma virus, may be used for delivery of nucleotide sequences encoding recombinant protein complex components into the targeted cell population. Methods which are well known to those skilled in the art can be used to construct recombinant viral vectors containing coding sequences. See, for example, the techniques described in Maniatis et al., 1989, Molecular Cloning A Laboratory Manual, Cold Spring Harbor Laboratory, N.Y. and Ausubel et al., 1989, Current Protocols in Molecular Biology, Greene Publishing Associates and Wiley Interscience, N.Y. Alternatively, recombinant nucleic acid molecules encoding protein sequences can be used as naked DNA or in reconstituted system e.g., liposomes or other lipid systems for delivery to target cells (See e.g., Felgner et al., 1989, Nature 337:387–8). *Pharmaceutical Formulations and Modes of Administration*

The particular compound, antibody, antisense or ribozyme molecule that affects the protein complexes and the disorder of interest can be administered to a patient either by themselves, or in pharmaceutical compositions where it is mixed with suitable carriers or excipient(s).

In treating a patient exhibiting an oncogenic disorder of interest, a therapeutically effective amount of a agent or agents such as these is administered. A therapeutically effective dose refers to that amount of the compound that results in amelioration of symptoms or a prolongation of survival in a patient.

Toxicity and therapeutic efficacy of such compounds can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Compounds which exhibit large therapeutic indices are preferred. The data obtained from these cell culture assays and animal studies can be used in formulating a range of dosage for use in human. The dosage of such compounds lies preferably within a range of circulating concentrations that include the $ED_{50}$ with little or no toxicity. The dosage may vary within this range depending upon the dosage form employed and the route of administration utilized.

For any compound used in the method of the invention, the therapeutically effective dose can be estimated initially from cell culture assays. For example, a dose can be formulated in animal models to achieve a circulating plasma concentration range that includes the $IC_{50}$ as determined in cell culture (i.e., the concentration of the test compound which achieves a half-maximal disruption of the protein complex, or a half-maximal inhibition of the cellular level and/or activity of a complex component). Such information can be used to more accurately determine useful doses in humans. Levels in plasma may be measured, for example, by HPLC.

The exact formulation, route of administration and dosage can be chosen by the individual physician in view of the patient's condition. (See e.g. Fingl et al., 1975, in "The Pharmacological Basis of Therapeutics", Ch. 1 p1).

It should be noted that the attending physician would know how to and when to terminate, interrupt, or adjust administration due to toxicity, or to organ dysfunctions. Conversely, the attending physician would also know to adjust treatment to higher levels if the clinical response were not adequate (precluding toxicity). The magnitude of an administrated dose in the management of the oncogenic disorder of interest will vary with the severity of the condition to be treated and to the route of administration. The severity of the condition may, for example, be evaluated, in part, by standard prognostic evaluation methods. Further, the dose and perhaps dose frequency, will also vary according to the age, body weight, and response of the individual patient. A program comparable to that discussed above may be used in veterinary medicine.

Depending on the specific conditions being treated, such agents may be formulated and administered systemically or locally. Techniques for formulation and administration may be found in "Remington's Pharmaceutical Sciences," 1990, 18th ed., Mack Publishing Co., Easton, Pa. Suitable routes may include oral, rectal, transdermal, vaginal, transmucosal, or intestinal administration; parenteral delivery, including intramuscular, subcutaneous, intramedullary injections, as well as intrathecal, direct intraventricular, intravenous, intraperitoneal, intranasal, or intraocular injections, just to name a few.

For injection, the agents of the invention may be formulated in aqueous solutions, preferably in physiologically compatible buffers such as Hanks's solution, Ringer's solution, or physiological saline buffer. For such transmucosal administration, penetrants appropriate to the barrier to be permeated are used in the formulation. Such penetrants are generally known in the art.

Use of pharmaceutically acceptable carriers to formulate the compounds herein disclosed for the practice of the invention into dosages suitable for systemic administration is within the scope of the invention. With proper choice of carrier and suitable manufacturing practice, the compositions of the present invention, in particular, those formulated as solutions, may be administered parenterally, such as by intravenous injection. The compounds can be formulated readily using pharmaceutically acceptable carriers well known in the art into dosages suitable for oral administration. Such carriers enable the compounds of the invention to be formulated as tablets, pills, capsules, liquids, gels, syrups, slurries, suspensions and the like, for oral ingestion by a patient to be treated.

Agents intended to be administered intracellularly may be administered using techniques well known to those of ordinary skill in the art. For example, such agents may be encapsulated into liposomes, then administered as described above. Liposomes are spherical lipid bilayers with aqueous interiors. All molecules present in an aqueous solution at the time of liposome formation are incorporated into the aqueous interior. The liposomal contents are both protected from the external microenvironment and, because liposomes fuse with cell membranes, are efficiently delivered into the cell cytoplasm. Additionally, due to their hydrophobicity, small organic molecules may be directly administered intracellularly.

Pharmaceutical compositions suitable for use in the present invention include compositions wherein the active ingredients are contained in an effective amount to achieve its intended purpose. Determination of the effective amounts is well within the capability of those skilled in the art, especially in light of the detailed disclosure provided herein.

In addition to the active ingredients, these pharmaceutical compositions may contain suitable pharmaceutically acceptable carriers comprising excipients and auxiliaries which facilitate processing of the active compounds into preparations which can be used pharmaceutically. The preparations formulated for oral administration may be in the form of tablets, dragees, capsules, or solutions.

The pharmaceutical compositions of the present invention may be manufactured in a manner that is itself known, e.g., by means of conventional mixing, dissolving, granulating, dragee-making, levigating, emulsifying, encapsulating, entrapping or lyophilizing processes.

Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

Pharmaceutical preparations for oral use can be obtained by combining the active compounds with solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate.

Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added.

Identification of Agents

The complexes, components of such complexes, functional equivalents thereof, and/or cell lines that express such components and exhibit such protein complexes may be used to screen for additional compounds, antibodies, or other molecules capable of modulating the signal transduction event such complexes are involved in. Methods for purifying and/or producing such complexes, components of the complexes, functional equivalents thereof, and/or cell lines are described herein. The compounds, antibodies, or other molecules identified may, for example, act to disrupt the protein complexes of the invention (i.e., decrease or inhibit interactions between component members of the complexes, thereby causing physical separation of the components, and/or perturbing the activity of the complexes) or may lower the cellular level and/or decrease the activity of one or more of the components of such complexes.

Such compounds may include, but are not limited to, peptides made of D- and/or L-configuration amino acids (in, for example, the form of random peptide libraries; see Lam, K. S. et al., 1991, Nature 354:82–84), phosphopeptides (in, for example, the form of random or partially degenerate, directed phosphopeptide libraries, see Songyang, Z. et al., 1993, Cell 767–778), antibodies, and small organic or inorganic molecules. Synthetic compounds, natural products, and other sources of potentially biologically active materials may be screened in a variety of ways, as described herein. The compounds, antibodies, or other molecules identified may be used as oncogenic disorder treatments, as described herein.

Compounds that bind to individual components, or functional portions of the individual components of the complexes (and may additionally be capable of disrupting complex formation) may be identified.

One such method included within the scope of the invention is a method for identifying an agent to be tested for an ability to modulate a signal transduction pathway disorder comprising:

(a) exposing at least one agent to a protein comprising a functional portion of a member of the roteine complex for a time sufficient to allow binding of the agent to the functional portion of the member;

(b) removing non-bound agents; and (c) determining the presence of the compound bound to the functional portion of the member of the protein complex, thereby identifying an agent to be tested for an ability to modulate a disorder involving a polypeptide complex.

By "signal transduction disorder" is meant any disease or condition associated with an abnormality in a signal transduction pathway. The protein complex referred to below is a physical association of a protein containing a BLM domain and its natural binding partner. The level of interaction between the two components of the complex may be abnormal and thus cause the abnormality in the signal transduction pathway. Alternatively, the level of interaction between the complex components may be normal, but affecting that interaction may effectively treat a signal transduction pathway disorder.

The term "protein" refers to a compound formed of 5–50 or more amino acids joined together by peptide bonds. An "amino acid" is a subunit that is polymerized to form proteins and there are twenty amino acids that are universally found in proteins. The general formula for an amino acid is $H_2N$—CHR—COOH, in which the R group can be anything from a hydrogen atom (as in the amino acid glycine) to a complex ring (as in the amino acid tryptophan).

A functional portion of an individual component of the complexes may be defined here as a protein portion of an individual component of a complex still capable of forming a stable complex with another member of the complex under standard cellular and physiological conditions. For example, a functional portion of a component may include, but is not limited to, a protein portion of the BLM domain which is still capable of stably binding a corresponding natural binding domain of an associated protein, and thus is still capable of forming a complex with that protein. Further, in the case of the catalytic domains of the individual components of the invention, a functional portion of a catalytic domain may refer to a protein still capable of stably binding a substrate molecule under standard physiological conditions.

One method utilizing this approach that may be pursued in the isolation of such complex component-binding molecules would include the attachment of a component molecule, or a functional portion thereof, to a solid matrix, such as agarose or plastic beads, microtiter wells, petri dishes, or membranes composed of, for example, nylon or nitrocellulose, and the subsequent incubation of the attached component molecule in the presence of a potential component-binding compound or compounds. Attachment to said solid support may be direct or by means of a component specific antibody bound directly to the solid support. After incubation, unbound compounds are washed away, component-bound compounds are recovered. By utilizing this procedure, large numbers of types of molecules may be simultaneously screened for complex component-binding activity.

The complex components which may be utilized in the above screening method may include, but are not limited to, molecules or functional portions thereof, such as catalytic domains, phosphorylation domains, extracellular domains, or portions of extracellular domains, such as ligand-binding domains, and adaptor proteins, or functional portions thereof. The peptides used may be phosphorylated, e.g., may contain at least one phosphorylated amino acid residue, preferably a phosphorylated Tyr amino acid residue, or may be unphosphorylated. A phosphorylation domain may be defined as a peptide region that is specifically phosphorylated at certain amino acid residues. A functional portion of such a phosphorylation domain may be defined as a peptide capable of being specifically phosphorylated at certain amino acids by a specific protein.

Molecules exhibiting binding activity may be further screened for an ability to disrupt protein complexes. Alternatively, molecules may be directly screened for an ability to promote the complexes. For example, in vitro complex formation may be assayed by, first, immobilizing one component, or a functional portion thereof, of the complex of interest to a solid support. Second, the immobilized complex component may be exposed to a compound such as one identified as above, and to the second component, or a functional portion thereof, of the complex of interest. Third, it may be determined whether or not the second component is still capable of forming a complex with the immobilized component in the presence of the compound. In addition, one could look for an increase in binding.

Additionally, complex formation in a whole cell may be assayed by utilizing co-immunoprecipitation techniques well known to those of skill in the art. Briefly, a cell line capable of forming a complex of interest may be exposed to a compound such as one identified as above, and a cell lysate may be prepared from this exposed cell line. An antibody raised against one of the components of the complex of interest may be added to the cell lysate, and subjected to standard immunoprecipitation techniques. In cases where a complex is still formed, the immunoprecipitation will precipitate the complex, whereas in cases where the complex has been disrupted, only the complex component to which the antibody is raised will be precipitated.

A preferred method for assessing modulation of complex formation within a cell utilizes a method similar to that described above. Briefly, a cell line capable of forming a complex of interest is exposed to a test compound. The cells are lysed and the lysate contacted with an antibody specific to one component of the complex, said antibody having been previously bound to a solid support. Unbound material is washed away, and the bound material is exposed to a second antibody, said second antibody binding specifically to a second component of the complex. The amount of second antibody bound is easily detected by techniques well known in the art. Cells exposed to an inhibitory test compound will have formed a lesser amount of complex compared to cells not exposed to the test compound, as measured by the amount of second antibody bound. Cells exposed to a test compound that promotes complex formation will have an increased amount of second antibody bound.

The effect of an agent on the transformation capability of the complex of interest may be directly assayed. Such agents may, but are not required to, include those agents identified by utilizing the above screening technique. For example, an agent or agents may be administered to a cell such as a breast cancer cell, capable of forming a complex, for example, which, in the absence of any inhibitory agent, would lead to the cell's transformation. The transformation state of the cell may then be measured in vitro, by monitoring, for example, its ability to form colonies in soft agar. Alternatively, a cell's transformation state may be monitored in vivo by, for example, determining its ability to form tumors in immunodeficient nude or severe combined immunodeficiency (SCID) mice.

Agents capable of disrupting complex formation and capable of reducing or inhibiting disorders, such as breast cancer, which involve the formation of such complexes may be used in the treatment of patients exhibiting or at risk for such disorders. A sufficient amount of agent or agents such as those described above may be administered to a patient so that the oncogenic capability of cells which, in the absence of such agents, would contain protein complexes, is reduced or eliminated.

Purification and Production of Complexes

Described in this Section are methods for the synthesis or recombinant expression of components, or fragments thereof, of the protein complexes of the invention. Also described herein are methods by which cells exhibiting the protein complexes of the invention may be engineered.

Purification Methods

The complexes of the invention may be substantially purified, i.e., may be purified away from at least 90% (on a weight basis), and from at least 99%, if desired, of other proteins, glycoproteins, and other macromolecules with which it is associated. Such purification can be achieved by utilizing a variety of procedures well known to those of skill in the art, such as subjecting cells, tissue or fluid containing the complex to a combination of standard methods, for example, ammonium sulfate precipitation, molecular sieve chromatography, and/or ion exchange chromatography.

Alternatively, or additionally, a complex may be purified by immunoaffinity chromatography using an immunoadsorbent column to which an antibody is immobilized which is capable of binding to one or more components of the complex. Such an antibody may be monoclonal or polyclonal in origin. Other useful types of affinity purification for the protein complex may utilize, for example, a solid-phase substrate which binds the catalytic kinase domain of a protein, or an immobilized binding site for noncatalytic domains of the components of the complex, which bind in such a manner as to not disrupt the complex.

The complex of the present invention may be biochemically purified from a variety of cell or tissue sources. For purification of a naturally occurring complex, cellular sources may include, for example, baculovirus-infected SF9 cells, A-431, CHO, and/or 3T3 cells. In a preferred embodiment of the present invention, the complex comprises the receptor GRB-7 or GRB-10 adaptor protein.

Synthesis and Expression Methods

Methods for the synthesis of polypeptides or fragments thereof, which are capable of acting as components of the complexes of the present invention, are well-known to those of ordinary skill in the art. See, for example, Creighton, 1983, Proteins: Structures and Molecular Principles, W. H. Freeman and Co., NY, which is incorporated herein, by reference, in its entirety.

Components of a complex which have been separately synthesized or recombinantly produced, may be reconstituted to form a complex by standard biochemical techniques well known to those skilled in the art. For example, samples containing the components of the complex may be combined in a solution buffered with greater than about 150 mM NaCl, at a physiological pH in the range of 7, at room temperature. For example, a buffer comprising 20 mM Tris-HCl, pH 7.4, 137 mMNaCl, 10% glycerol, 1% Triton X-100, 0.1% SDS, 0.5% deoxycholate and 2 mM EDTA could be used.

Methods for preparing the components of complexes of the invention by expressing nucleic acid encoding proteins are described herein. Methods which are well known to those skilled in the art can be used to construct expression vectors containing protein coding sequences and appropriate transcriptional/translational control signals. These methods include, for example, in vitro recombinant DNA techniques, synthetic techniques and in vivo recombination/genetic recombination. DNA and RNA synthesis may, additionally, be performed using an automated synthesizers. See, for example, the techniques described in Maniatis et al., 1989, Molecular Cloning A Laboratory Manual, Cold Spring Harbor Laboratory, N.Y. and Ausubel et al., 1989, Current Protocols in Molecular Biology, Greene Publishing Associates and Wiley Interscience, N.Y.

A variety of host-expression vector systems may be utilized to express the coding sequences of the components of the complexes of the invention. Such host-expression systems represent vehicles by which the coding sequences of interest may be produced, but also represent cells which may, when transformed or transfected with the appropriate nucleotide coding sequences, exhibit the protein complexes of the invention. These include but are not limited to microorganisms such as bacteria (e.g., *E.coli, B. subtilis*) transformed with recombinant bacteriophage DNA, plasmid DNA or cosmid DNA expression vectors containing protein coding sequences; yeast (e.g., Saccharomyces and Pichia) transformed with recombinant yeast expression vectors containing the protein coding sequences; insect cell systems infected with recombinant virus expression vectors (e.g., baculovirus) containing the protein coding sequences; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing the protein coding sequences coding sequence; or mammalian cell systems (e.g., COS, CHO, BHK, 293, 3T3) harboring recombinant expression constructs containing promoters derived from the genome of mammalian cells (e.g., metallothionein promoter) or from mammalian viruses (e.g., the adenovirus late promoter; the vaccinia virus 7.5K promoter).

In bacterial systems a number of expression vectors may be advantageously selected depending upon the use intended for the complex being expressed. For example, when large quantities of complex proteins are to be produced for the generation of antibodies or to screen peptide libraries, vectors which direct the expression of high levels of fusion protein products that are readily purified may be desirable. Such vectors include but are not limited to the *E. coli* expression vector pUR278 (Ruther et al., 1983, EMBO J. 2:1791), in which the protein coding sequence may be ligated individually into the vector in frame with the lac Z coding region so that a fusion protein is produced; pIN vectors (Inouye & Inouye, 1985, Nucleic acids Res. 13:3101–3109; Van Heeke & Schuster, 1989, J. Biol. Chem. 264:5503–5509); and the like. pGEX vectors may also be used to express foreign polypeptides as fusion proteins with glutathione S-transferase (GST). In general, such fusion proteins are soluble and can easily be purified from lysed cells by adsorption to glutathione-agarose beads followed by elution in the presence of free glutathione. The pGEX vectors are designed to include thrombin or factor Xa protease cleavage sites so that the cloned protein can be released from the GST moiety.

In an insect system, *Autographa californica* nuclear polyhedrosis virus (AcNPV) is used as a vector to express foreign genes. The virus grows in *Spodoptera frugiperda* cells. The complex coding sequence may be cloned individually into non-essential regions (for example the polyhedrin gene) of the virus and placed under control of an AcNPV promoter (for example the polyhedrin promoter). Successful insertion of the PTK/adaptor complex coding sequence will result in inactivation of the polyhedrin gene and production of non-occluded recombinant virus (i.e., virus lacking the proteinaceous coat coded for by the polyhedrin gene). These recombinant viruses are then used to infect *Spodoptera frugiperda* cells in which the inserted gene is expressed (e.g., see Smith et al., 1983, J. Viol. 46:584; Smith, U.S. Pat. No. 4,215,051).

In mammalian host cells, a number of viral based expression systems may be utilized. In cases where an adenovirus is used as an expression vector, the complex coding sequence may be ligated to an adenovirus transcription/translation control complex, e.g., the late promoter and tripartite leader sequence. This chimeric gene may then be inserted in the adenovirus genome by in vitro or in vivo recombination. Insertion in a non-essential region of the viral genome (e.g., region E1 or E3) will result in a recombinant virus that is viable and capable of expressing proteins in infected hosts. (E.g., See Logan & Shenk, 1984, Proc. Natl. Acad. Sci. USA 81:3655–3659). Specific initiation signals may also be required for efficient translation of inserted coding sequences. These signals include the ATG initiation codon and adjacent sequences.

In cases where an entire protein gene, including its own initiation codon and adjacent sequences, is inserted into the appropriate expression vector, no additional translational control signals may be needed. However, in cases where only a portion of the coding sequence is inserted, exogenous translational control signals, including the ATG initiation codon, must be provided. Furthermore, the initiation codon must be in phase with the reading frame of the desired coding sequence to ensure translation of the entire insert. These exogenous translational control signals and initiation codons can be of a variety of origins, both natural and synthetic. The efficiency of expression may be enhanced by the inclusion of appropriate transcription enhancer elements, transcription terminators, etc. (see Bittner et al., 1987, Methods in Enzymol. 153:516–544).

In addition, a host cell strain may be chosen which modulates the expression of the inserted sequences, or modifies and processes the gene product in the specific fashion desired. Such modifications (e.g., glycosylation) and processing (e.g., cleavage) of protein products may be important for the function of the protein. Different host cells have characteristic and specific mechanisms for the post-translational processing and modification of proteins. Appropriate cells lines or host systems can be chosen to ensure the correct modification and processing of the foreign protein expressed. To this end, eukaryotic host cells which possess the cellular machinery for proper processing of the primary transcript, glycosylation, and phosphorylation of the gene product may be used. Such mammalian host cells include but are not limited to CHO, VERO, BHK, HeLa, COS, MDCK, 293, 3T3, WI38, etc.

For long-term, high-yield production of recombinant proteins, stable expression is preferred. For example, cell lines which stably coexpress both the proteins may be engineered. Rather than using expression vectors which contain viral origins of replication, host cells can be transformed with the protein encoding DNA independently or coordinately controlled by appropriate expression control elements (e.g., promoter, enhancer, sequences, transcription terminators, polyadenylation sites, etc.), and a selectable marker.

Following the introduction of foreign DNA, engineered cells may be allowed to grow for 1–2 days in an enriched media, and then are switched to a selective media. The selectable marker in the recombinant plasmid confers resistance to the selection and allows cells to stably integrate the plasmid into their chromosomes and grow to form foci which in turn can be cloned and expanded into cell lines. This method may advantageously be used to engineer cell lines which coexpress both the PTK and adaptor protein. Such engineered cell lines are particularly useful in screening and evaluation of compounds that affect signals mediated by the complexes.

A number of selection systems may be used, including but not limited to the herpes simplex virus thymidine kinase (Wigler, et al., 1977, Cell 11:223), hypoxanthine-guanine phosphoribosyltransferase (Szybalska & Szybalski, 1962, Proc. Natl. Acad. Sci. USA 48:2026), and adenine phosphoribosyltransferase (Lowy, et al., 1980, Cell 22:817) genes can be employed in tk⁻, hgprt⁻ or aprt⁻ cells, respectively. Also, antimetabolite resistance can be used as the basis of selection for dhfr, which confers resistance to methotrexate (Wigler, et al., 1980, Natl. Acad. Sci. USA 77:3567; O'Hare, et al., 1981, Proc. Natl. Acad. Sci. USA 78:1527); gpt, which confers resistance to mycophenolic acid (Mulligan & Berg, 1981), Proc. Natl. Acad. Sci. USA 78:2072); neo, which confers resistance to the aminoglycoside G-418 (Colberre-Garapin, et al., 1981, J. Mol. Biol. 150:1); and hygro, which confers resistance to hygromycin (Santerre, et al., 1984, Gene 30:147) genes.

New members of the protein families capable of forming the complexes of the invention may be identified and isolated by molecular biological techniques well known in the art. For example, a previously unknown protein encoding gene may be isolated by performing a polymerase chain reaction (PCR) using two degenerate oligonucleotide primer pools designed on the basis of highly conserved sequences within domains common to members of the protein family. The template for the reaction may be cDNA obtained by reverse transcription of mRNA prepared from cell lines or tissue known to express complexes. The PCR product may be subcloned and sequenced to insure that the amplified sequences represent the sequences of a member of the PTK or adaptor subfamily. The PCR fragment may then be used to isolate a full length protein cDNA clone by radioactively labeling the amplified fragment and screening a bacteriophage cDNA library. Alternatively, the labeled fragment may be used to screen a genomic library. For a review of cloning strategies which may be used, see e.g., Maniatis, 1989, Molecular Cloning, A Laboratory Manual, Cold Springs Harbor Press, N.Y.; and Ausubel et al., 1989, Current Protocols in Molecular Biology, (Green Publishing Associates and Wiley Interscience, N.Y.).

A general method for cloning previously unknown proteins has been described by Skolnik (Skolnik, E. Y., 1991, Cell 65:75) and Skolnik et al., (U.S. patent application Ser. No. 07/643,237) which are incorporated herein, by reference, in their entirety, including drawings. Briefly, new members of the family of proteins may be identified by their ability to specifically bind to at least a portion of a BLM domain in a peptide.

Derivatives of Complexes

Also provided herein are functional derivatives of a complex. By "functional derivative" is meant a "chemical derivative," "fragment," "variant," "chimera," or "hybrid" of the complex, which terms are defined below. A functional derivative retains at least a portion of the function of the protein, for example reactivity with an antibody specific for the complex, enzymatic activity or binding activity mediated through noncatalytic domains, which permits its utility in accordance with the present invention.

A "chemical derivative" of the complex contains additional chemical moieties not normally a part of the protein. Covalent modifications of the protein complex or peptides are included within the scope of this invention. Such modifications may be introduced into the molecule by reacting targeted amino acid residues of the peptide with an organic derivatizing agent that is capable of reacting with selected side chains or terminal residues, as described below.

Cysteinyl residues most commonly are reacted with alpha-haloacetates (and corresponding amines), such as chloroacetic acid or chloroacetamide, to give carboxymethyl or carboxyamidomethyl derivatives. Cysteinyl residues also are derivatized by reaction with bromotrifluoroacetone, α-bromo-β(5-imidozoyl)propionic acid, chloroacetyl phosphate, N-alkylmaleimides, 3-nitro-2-pyridyl disulfide, methyl 2-pyridyl disulfide, p-chloromercuribenzoate, 2-chloromercuri-4-nitrophenol, or chloro-7-nitrobenzo-2-oxa-1,3-diazole.

Histidyl residues are derivatized by reaction with diethylprocarbonate at pH 5.5–7.0 because this agent is relatively specific for the histidyl side chain. Parabromophenacyl bromide also is useful; the reaction is preferably performed in 0.1 M sodium cacodylate at pH 6.0.

Lysinyl and amino terminal residues are reacted with succinic or other carboxylic acid anhydrides. Derivatization with these agents has the effect or reversing the charge of the lysinyl residues. Other suitable reagents for derivatizing α-amino-containing residues include imidoesters such as methyl picolinimidate; pyridoxal phosphate; pyridoxal; chloroborohydride; trinitrobenzenesulfonic acid; O-methylisourea; 2,4 pentanedione; and transaminase-catalyzed reaction with glyoxylate.

Arginyl residues are modified by reaction with one or several conventional reagents, among them phenylglyoxal, 2,3-butanedione, 1,2-cyclohexanedione, and ninhydrin. Derivatization of arginine residues requires that the reaction be performed in alkaline conditions because of the high $pK_a$ of the guanidine functional group. Furthermore, these reagents may react with the groups of lysine as well as the arginine ε-amino group.

Tyrosyl residues are well-known targets of modification for introduction of spectral labels by reaction with aromatic diazonium compounds or tetranitromethane. Most commonly, N-acetylimidizol and tetranitromethane are used to form O-acetyl tyrosyl species and 3-nitro derivatives, respectively.

Carboxyl side groups (aspartyl or glutamyl) are selectively modified by reaction carbodiimide (R'—N—C—N—R') such as 1-cyclohexyl-3-(2-morpholinyl(4-ethyl) carbodiimide or 1-ethyl-3-(4-azonia-4,4-dimethylpentyl) carbodiimide. Furthermore, aspartyl and glutamyl residue are converted to asparaginyl and glutaminyl residues by reaction with ammonium ions.

Glutaminyl and asparaginyl residues are frequently deamidated to the corresponding glutamyl and aspartyl residues. Alternatively, these residues are deamidated under mildly acidic conditions. Either form of these residues falls within the scope of this invention.

Derivatization with bifunctional agents is useful, for example, for cross-linking the component peptides of the complexes to each other or the complex to a water-insoluble support matrix or to other macromolecular carriers. Commonly used cross-linking agents include, for example, 1,1-bis(diazoacetyl)-2-phenylethane, glutaraldehyde, N-hydroxysuccinimide esters, for example, esters with 4-azidosalicylic acid, homobifunctional imidoesters, including disuccinimidyl esters such as 3,3'-dithiobis (succinimidylpropionate), and bifunctional maleimides such as bis-N-maleimido-1,8-octane. Derivatizing agents such as methyl-3-[p-azidophenyl) dithiolpropioimidate yield photo-activatable intermediates that are capable of forming crosslinks in the presence of light. Alternatively, reactive water-insoluble matrices such as cyanogen bromide-activated carbohydrates and the reactive substrates described in U.S. Pat. Nos. 3,969,287; 3,691,016; 4,195, 128; 4,247,642; 4,229,537; and 4,330,440 are employed for protein immobilization.

Other modifications include hydroxylation of proline and lysine, phosphorylation of hydroxyl groups of seryl or threonyl residues, methylation of the alpha-amino groups of lysine, arginine, and histidine side chains (Creighton, T. E., Proteins: Structure and Molecular Properties, W. H. Freeman & Co., San Francisco, pp. 79–86 (1983)), acetylation of the Nterminal amine, and, in some instances, amidation of the C-terminal carboxyl groups.

Such derivatized moieties may improve the stability, solubility, absorption, biological half life, and the like. The moieties may alternatively eliminate or attenuate any undesirable side effect of the protein complex and the like. Moieties capable of mediating such effects are disclosed, for example, in Remington's Pharmaceutical Sciences, 18th ed., Mack Publishing Co., Easton, Pa. (1990).

The term "fragment" is used to indicate a polypeptide derived from the amino acid sequence of the proteins, of the complexes having a length less than the full-length polypeptide from which it has been derived. Such a fragment may, for example, be produced by proteolytic cleavage of the full-length protein. Preferably, the fragment is obtained recombinantly by appropriately modifying the DNA sequence encoding the proteins to delete one or more amino acids at one or more sites of the C-terminus, N-terminus, and/or within the native sequence.

Fragments of a protein, when present in a complex resembling the naturally occurring complex, are useful for screening for compounds that act to modulate signal transduction, as described below. It is understood that such fragments, when present in a complex may retain one or more characterizing portions of the native complex. Examples of such retained characteristics include: catalytic activity; substrate specificity; interaction with other molecules in the intact cell; regulatory functions; or binding with an antibody specific for the native complex, or an epitope thereof.

Another functional derivative intended to be within the scope of the present invention is a complex comprising at least one "variant" polypeptide which either lack one or more amino acids or contain additional or substituted amino acids relative to the native polypeptide. The variant may be derived from a naturally occurring complex component by appropriately modifying the protein DNA coding sequence to add, remove, and/or to modify codons for one or more amino acids at one or more sites of the C-terminus, N-terminus, and/or within the native sequence. It is understood that such variants having added, substituted and/or additional amino acids retain one or more characterizing portions of the native complex, as described above.

A functional derivative of complexes comprising proteins with deleted, inserted and/or substituted amino acid residues may be prepared using standard techniques well-known to those of ordinary skill in the art. For example, the modified components of the functional derivatives may be produced using site-directed mutagenesis techniques (as exemplified by Adelman et al., 1983, DNA 2:183) wherein nucleotides in the DNA coding the sequence are modified such that a modified coding sequence is modified, and thereafter expressing this recombinant DNA in a prokaryotic or eukaryotic host cell, using techniques such as those described above. Alternatively, components of functional derivatives of complexes with amino acid deletions, insertions and/or substitutions may be conveniently prepared by direct chemical synthesis, using methods well-known in the art. The functional derivatives of the complexes typically exhibit the same qualitative biological activity as the native complexes.

Evaluation of Disorders

The protein complexes of the invention involved in disorders may be utilized in developing a prognostic evaluation of the condition of a patient suspected of exhibiting such a disorder. For example, biological samples obtained from patients suspected of exhibiting a disorder involving a protein complex may be assayed for the presence of such complexes. If such a protein complex is normally present, and the development of the disorder is caused by an abnormal quantity of the complex, the assay should compare complex levels in the biological sample to the range expected in normal tissue of the same cell type.

Among the assays which may be undertaken may include, but are not limited to isolation of the protein complex of interest from the biological sample, or assaying for the presence of the complex by exposing the sample to an antibody specific for the complex, but non-reactive to any single, non-complexed component, and detecting whether antibody has specifically bound.

Alternatively, one or more of the components of the protein complex may be present in an abnormal level or in a modified form, relative to the level or form expected is normal, nononcogenic tissue of the same cell type. It is possible that overexpression of both components may indicate a particularly aggressive disorder. Thus, an assessment of the individual and levels of mRNA and protein in diseased tissue cells may provide valuable clues as to the course of action to be undertaken in treatment of such a disorder. Assays of this type are well known to those of skill in the art, and may include, but are not limited to, Northern blot analysis, RNAse protection assays, and PCR for determining mRNA levels. Assays determining protein levels are also well known to those of skill in the art, and may include, but are not limited to, Western blot analysis, immunoprecipitation, and ELISA analysis. Each of these techniques may also reveal potential differences in the form (e.g., the primary, secondary, or tertiary amino acid sequence, and/or post-translational modifications of the sequence) of the component(s).

Other embodiments are within the following claims.

What is claimed is:

1. An isolated or purified peptide consisting of a BLM domain, wherein said BLM domain consists of an amino acid sequence which has at least 20% sequence identity to amino acids 95 to 428 of GRB-7 as set forth in SEQ ID NO: 1.

2. The peptide of claim 1, wherein said peptide is produced recombinantly.

3. A composition comprising the peptide of claim 1, and a pharmaceutically acceptable carrier or diluent.

4. An isolated or purified peptide consisting of a BLM domain, wherein said BLM domain consists of an amino acid sequence that has at least 30% sequence similarity to amino acids 95 to 428 of GRB-7 as set forth in SEQ ID NO: 1.

5. An isolated or purified polypeptide consisting of a BLM domain, wherein said BLM domain consists of an amino acid sequence which has at least 20% sequence identity to amino acids 189 to 514 of GRB-10 as set forth in SEQ ID NO: 2.

6. The polypeptide of claim 5, wherein said polypeptide is produced recombinantly.

7. A composition comprising the polypeptide of claim 5 and a pharmaceutically acceptable carrier or diluent.

8. An isolated or purified polypeptide consisting of a BLM domain, wherein said BLM domain consists of an amino acid sequence that has at least 30% sequence similarity to amino acids 189 to 514 of GRB-10 as set forth in SEQ ID NO: 2.

* * * * *